United States Patent
Sanders

(10) Patent No.: US 9,283,057 B2
(45) Date of Patent: Mar. 15, 2016

(54) SYSTEM, APPARATUS AND METHOD FOR IMPLEMENTING IMPLANTS

(75) Inventor: Daniel Sanders, West Orange, NJ (US)

(73) Assignee: MID CORP., West Orange, NJ (US)

(*) Notice: Subject to any disclaimer, the term of this patent is extended or adjusted under 35 U.S.C. 154(b) by 33 days.

(21) Appl. No.: 13/981,754

(22) PCT Filed: Feb. 1, 2012

(86) PCT No.: PCT/US2012/023436
§ 371 (c)(1),
(2), (4) Date: Jul. 25, 2013

(87) PCT Pub. No.: WO2012/106397
PCT Pub. Date: Aug. 9, 2012

(65) Prior Publication Data
US 2013/0309632 A1      Nov. 21, 2013

Related U.S. Application Data

(60) Provisional application No. 61/438,681, filed on Feb. 2, 2011.

(51) Int. Cl.
*A61C 8/00* (2006.01)
*A61C 1/08* (2006.01)

(52) U.S. Cl.
CPC .............. *A61C 8/0068* (2013.01); *A61C 1/084* (2013.01); *A61C 8/0022* (2013.01); *A61C 8/0043* (2013.01); *A61C 8/0089* (2013.01); *A61C 8/0087* (2013.01)

(58) Field of Classification Search
CPC ........ A61C 8/00; A61C 8/001; A61C 8/0018; A61C 8/0019; A61C 8/0021; A61C 8/0022–8/0025; A61C 8/0036; A61C 8/0037; A61C 8/0042; A61C 8/0043; A61C 8/005; A61C 8/0053; A61C 8/0059; A61C 8/0063; A61C 8/0066; A61C 8/0068; A61C 8/0072; A61C 8/0075; A61C 8/0089; A61C 8/006; A61C 8/0069; A61B 17/7059
USPC ....................... 433/172–176, 201.1
See application file for complete search history.

(56) References Cited

U.S. PATENT DOCUMENTS 3,955,280 A      5/1976   Sneer
4,682,951 A *    7/1987   Linkow .................. A61C 8/001
                                                                 433/173

(Continued)

FOREIGN PATENT DOCUMENTS

CA          2416348 A1 *   7/2004   ............. A61C 8/001
ES    WO 2006136637 A2 *  12/2006   ........... A61C 8/0018

(Continued)

OTHER PUBLICATIONS

International Search Report dated Jul. 20, 2010 for Corresponding PCT Application No. IB2010/50456 filed Feb. 2, 2010, Published as 2010/089698 on Aug. 12, 2010.

(Continued)

*Primary Examiner* — Cris L Rodriguez
*Assistant Examiner* — Matthew Saunders
(74) *Attorney, Agent, or Firm* — The Dobrusin Law Firm, P.C.

(57) ABSTRACT

Systems, apparatuses, devices, kits and processes are provided to enhance bone implants. The bone implant includes one or more bone attachment components for securing the implant into a bone and a head component independent of and separable from the bone attachment components. In one embodiment, each bone attachment component includes an internally threaded bore hole sleeve for receiving a connector component. The head component preferably is adapted so as to be secured to the one or more bone attachment components at the time of initial implantation of the one or more bone attachment components and the head component into the bone. The head component preferably is adapted to be oriented relative to at least one of the one or more bone attachment components at a predetermined tilt angle, so that the implant generally conforms with a natural root structure of a missing tooth.

15 Claims, 17 Drawing Sheets

(56) References Cited

U.S. PATENT DOCUMENTS

| | | | |
|---|---|---|---|
| 4,713,077 A | 12/1987 | Small | |
| 5,116,337 A | 5/1992 | Johnson | |
| 5,196,016 A * | 3/1993 | Buser | A61B 17/8033 606/76 |
| 5,513,989 A * | 5/1996 | Crisio | A61C 8/0086 433/173 |
| 5,569,251 A * | 10/1996 | Baker | A61B 17/80 606/281 |
| 5,727,942 A | 3/1998 | Hartmann et al. | |
| 5,829,977 A | 11/1998 | Rogers et al. | |
| 5,863,200 A * | 1/1999 | Hamada | A61C 8/0048 433/173 |
| 5,871,486 A | 2/1999 | Huebner et al. | |
| 5,954,769 A | 9/1999 | Rosenlicht | |
| 6,017,345 A | 1/2000 | Richelsoph | |
| RE36,689 E | 5/2000 | Beaty et al. | |
| 6,068,478 A | 5/2000 | Grande et al. | |
| 6,093,023 A | 7/2000 | Sala Meseguer | |
| 6,123,546 A | 9/2000 | Bergstrom et al. | |
| 6,250,924 B1 | 6/2001 | Luotio | |
| 6,419,491 B1 | 7/2002 | Ricci et al. | |
| 6,527,554 B2 | 3/2003 | Hurson et al. | |
| 6,776,781 B1 * | 8/2004 | Uwaydah | A61B 17/7059 606/279 |
| 6,854,972 B1 | 2/2005 | Elian | |
| 6,863,529 B2 | 3/2005 | Strong et al. | |
| 7,048,739 B2 * | 5/2006 | Konieczynski | A61B 17/8038 606/288 |
| 7,097,451 B2 | 8/2006 | Tang | |
| 7,108,511 B1 | 9/2006 | Shatkin | |
| 7,291,013 B2 | 11/2007 | Aravena et al. | |
| 7,481,829 B2 * | 1/2009 | Baynham | A61B 17/686 606/289 |
| 7,621,913 B2 | 11/2009 | Semet | |
| 7,704,076 B2 | 4/2010 | Mullaly et al. | |
| 7,798,812 B2 | 9/2010 | Last-Pollak | |
| 7,806,685 B1 | 10/2010 | Grant | |
| 7,959,439 B2 | 6/2011 | Bulloch et al. | |
| 8,231,388 B2 | 7/2012 | Grant | |
| 8,287,278 B2 | 10/2012 | Grant | |
| 8,622,739 B2 * | 1/2014 | Karmon | A61B 17/025 433/173 |
| 8,900,277 B2 * | 12/2014 | Perrow | A61B 17/7059 606/280 |
| 2003/0082498 A1 | 5/2003 | Halldin et al. | |
| 2003/0180686 A1 | 9/2003 | Simmons | |
| 2003/0199876 A1 * | 10/2003 | Brace | A61B 17/8047 606/281 |
| 2003/0232308 A1 * | 12/2003 | Simmons, Jr. | A61C 8/0031 433/173 |
| 2004/0006346 A1 | 1/2004 | Holmen et al. | |
| 2004/0013999 A1 | 1/2004 | Sussman | |
| 2005/0100863 A1 | 5/2005 | Chang | |
| 2005/0287497 A1 * | 12/2005 | Carter | A61C 8/005 433/173 |
| 2006/0154205 A1 * | 7/2006 | Reggie | A61C 8/001 433/173 |
| 2006/0189991 A1 * | 8/2006 | Bickley | A61B 17/864 606/916 |
| 2007/0059666 A1 | 3/2007 | Zickman et al. | |
| 2008/0038694 A1 | 2/2008 | Tache et al. | |
| 2008/0113316 A1 * | 5/2008 | Menke | 433/174 |
| 2008/0124675 A1 * | 5/2008 | Adams | 433/174 |
| 2008/0140130 A1 * | 6/2008 | Chan | A61B 17/1728 606/280 |
| 2008/0227057 A1 * | 9/2008 | Anitua Aldecoa | 433/174 |
| 2008/0293012 A1 | 11/2008 | Chaves et al. | |
| 2009/0011382 A1 | 1/2009 | Bavar | |
| 2009/0171396 A1 * | 7/2009 | Baynham | A61B 17/686 606/280 |
| 2009/0202959 A1 | 8/2009 | Ajlouni et al. | |
| 2009/0204155 A1 | 8/2009 | Aschmann | |
| 2009/0258329 A1 * | 10/2009 | Adams | A61C 8/001 433/174 |
| 2009/0286202 A1 | 11/2009 | Ford et al. | |
| 2010/0003635 A1 | 1/2010 | Feith | |
| 2010/0003638 A1 | 1/2010 | Collins et al. | |
| 2010/0003639 A1 * | 1/2010 | Salvi et al. | 433/174 |
| 2010/0055646 A1 * | 3/2010 | Zhao | 433/174 |
| 2010/0145397 A1 * | 6/2010 | Overes | A61B 17/68 606/319 |
| 2010/0305613 A1 | 12/2010 | Abdelgany et al. | |
| 2010/0312280 A1 * | 12/2010 | Overes | A61B 17/68 606/264 |
| 2011/0151400 A1 | 6/2011 | Boiangiu et al. | |
| 2011/0151408 A1 | 6/2011 | Grant | |
| 2011/0159455 A1 | 6/2011 | Stumpel | |
| 2012/0122057 A1 * | 5/2012 | Adams | A61C 8/001 433/174 |

FOREIGN PATENT DOCUMENTS

| | | | | |
|---|---|---|---|---|
| GB | 2495429 A | | 4/2013 | |
| IT | WO 2006082610 A2 * | | 8/2006 | A61C 1/085 |
| WO | 2006/082610 A2 | | 8/2006 | |
| WO | WO 2008125049 A1 * | | 10/2008 | |
| WO | 2009/002154 A1 | | 12/2008 | |
| WO | 2009/115617 A1 | | 9/2009 | |
| WO | 2010/061124 A2 | | 6/2010 | |
| WO | 2010/089698 A2 | | 8/2010 | |
| WO | WO 2010089698 A2 * | | 8/2010 | A61C 1/084 |
| WO | 2012/106397 A1 | | 8/2012 | |

OTHER PUBLICATIONS

Written Opinion dated Jul. 20, 2010 for Corresponding PCT Application No. IB2010/50456 filed Feb. 2, 2010, Published as 2010/089698 on Aug. 12, 2010.

International Preliminary Report on Patentability dated Jul. 20, 2010 for Corresponding PCT Application No. IB2010/50456 filed Feb. 1, 2010, Published as 2010/089698 on Aug. 12, 2010.

International Search Report and Written Opinion, dated Jul. 13, 2012, PCT/US12/023436, filed Feb. 1, 2012.

International Preliminary Report on Patentability date Aug. 15, 2013 for PCT/US2012/023436, filed Feb. 1, 2012.

Bergkvist et al., A Finite Element Analysis of Stress Distribution in Bone Tissue Surrounding Uncoupled or Splinted Dental Implants, Clinical Implant Dentistry and Related Research. Nov. 2008, 40-46, 10(1), Blackwell Publishing.

Lobbezzo et al., Dental implants in patients with bruxing habits, Journal of Oral Rehabilitation, 2006, 152-159, 33, Blackwell Publishing Ltd.

Office Action from the UK Intellectual Property Office for copending patent application No. GB13040950.7, dated Aug. 13, 2013.

* cited by examiner

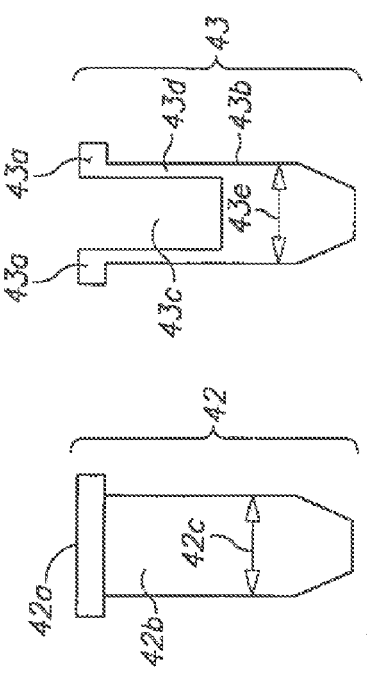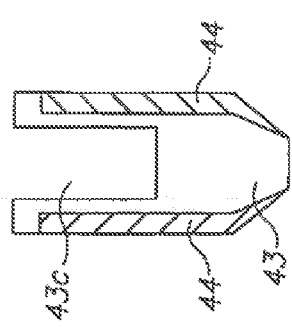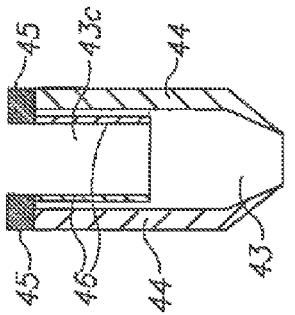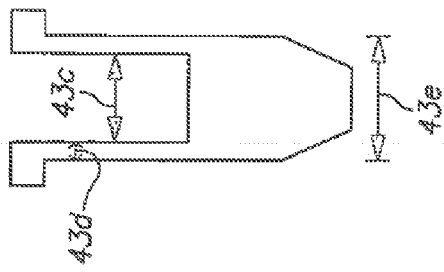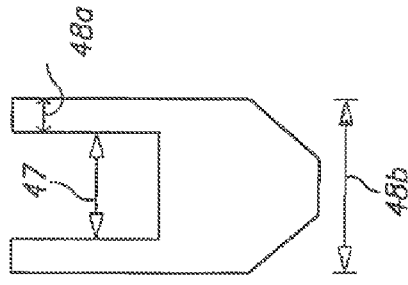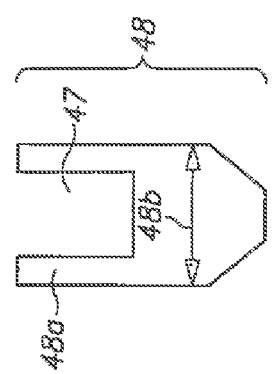

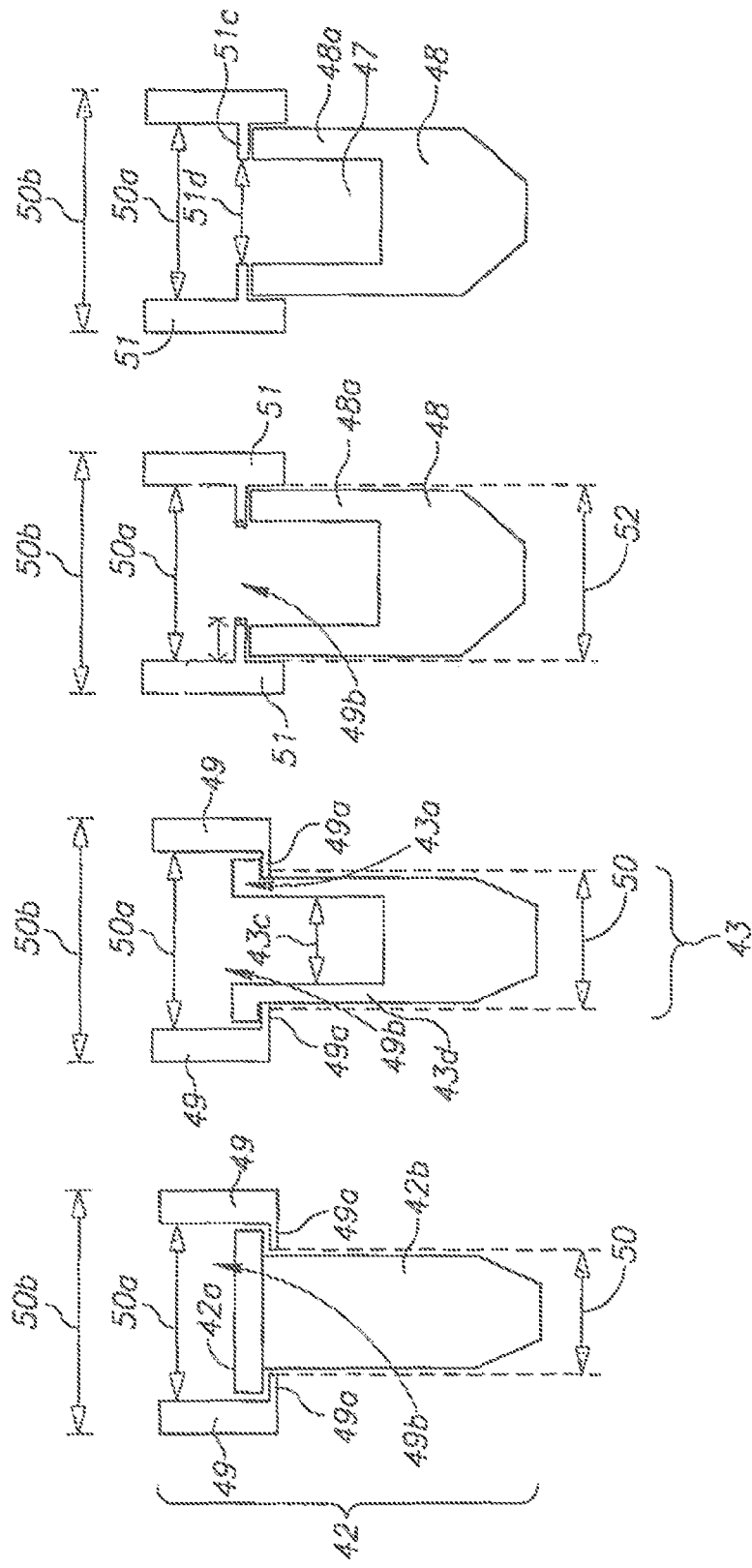

PCT/IB 2010/050456

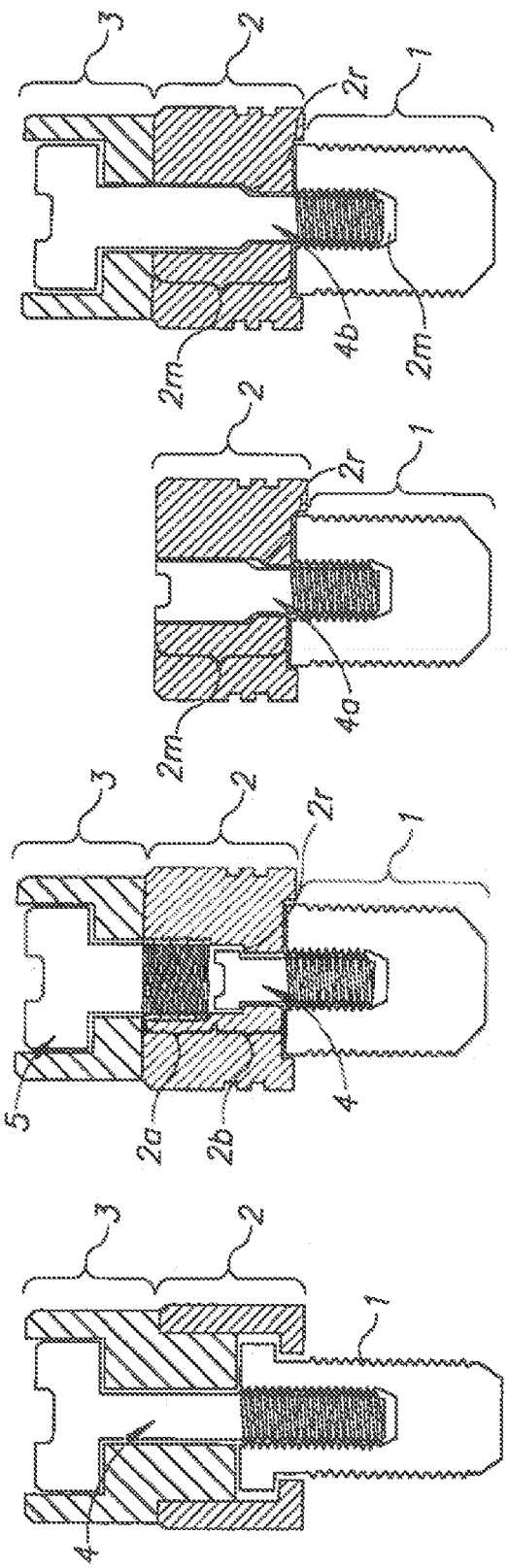

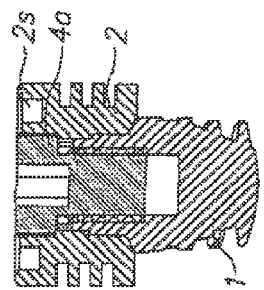
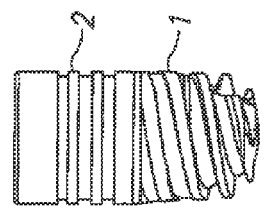
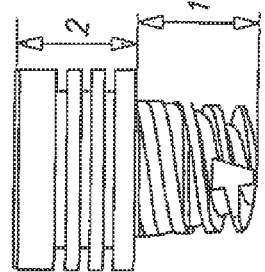
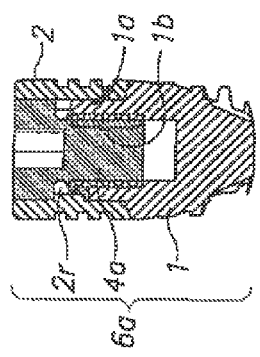
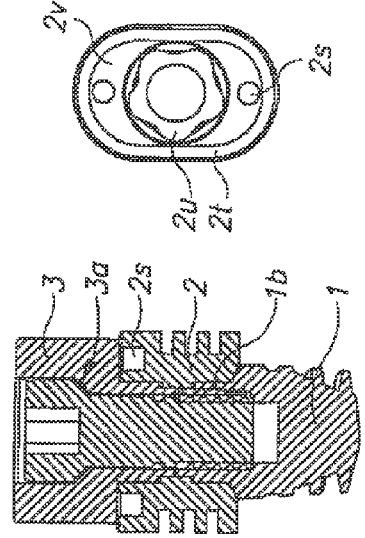
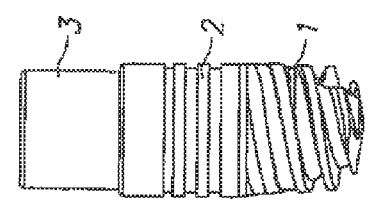
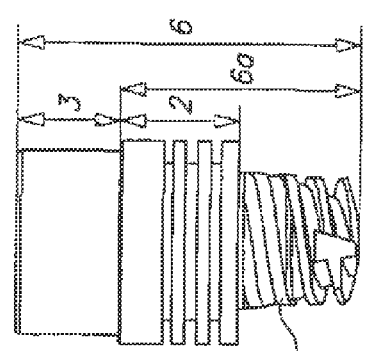
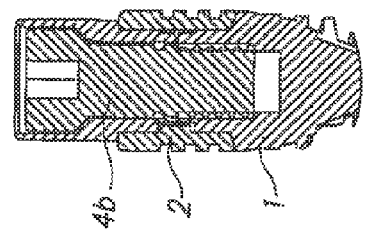
FIG.5A  FIG.5B  FIG.5C  FIG.5D
FIG.5E  FIG.5F  FIG.5G  FIG.5H  FIG.5I

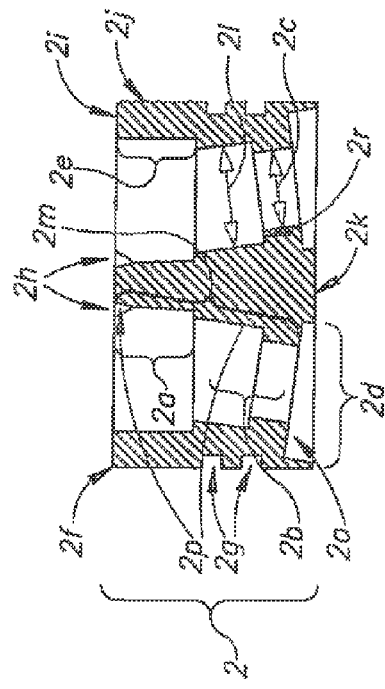
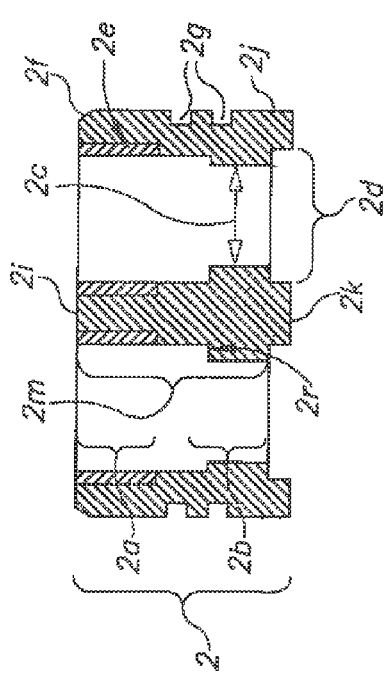
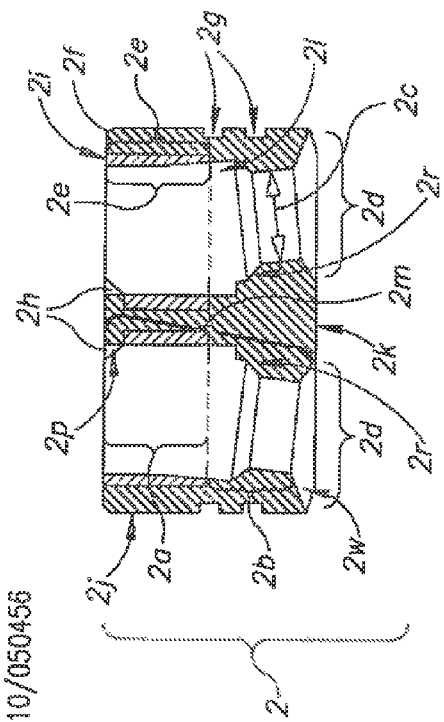

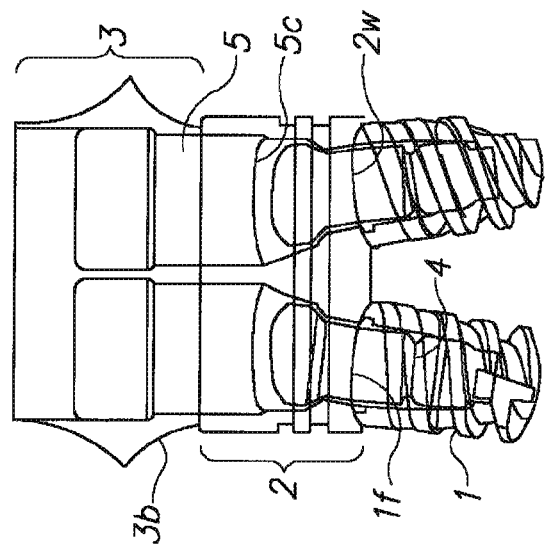
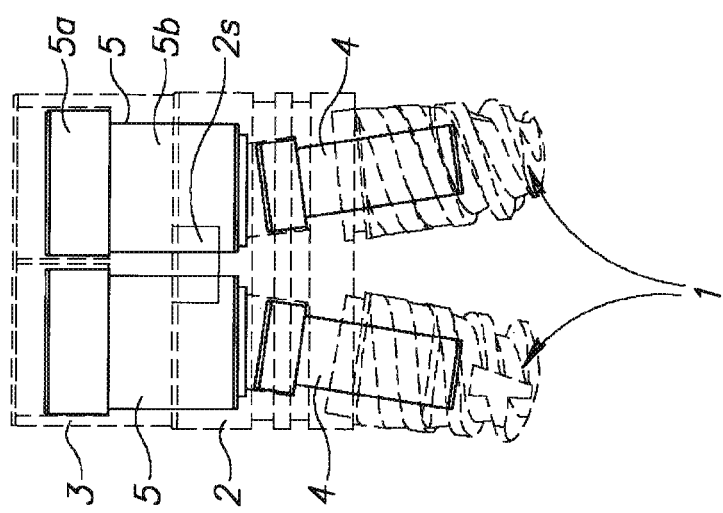
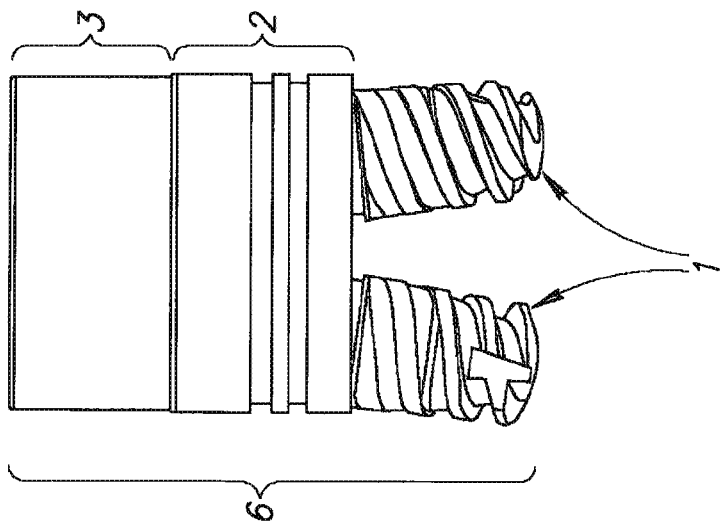
FIG.8A
FIG.8B
FIG.8C

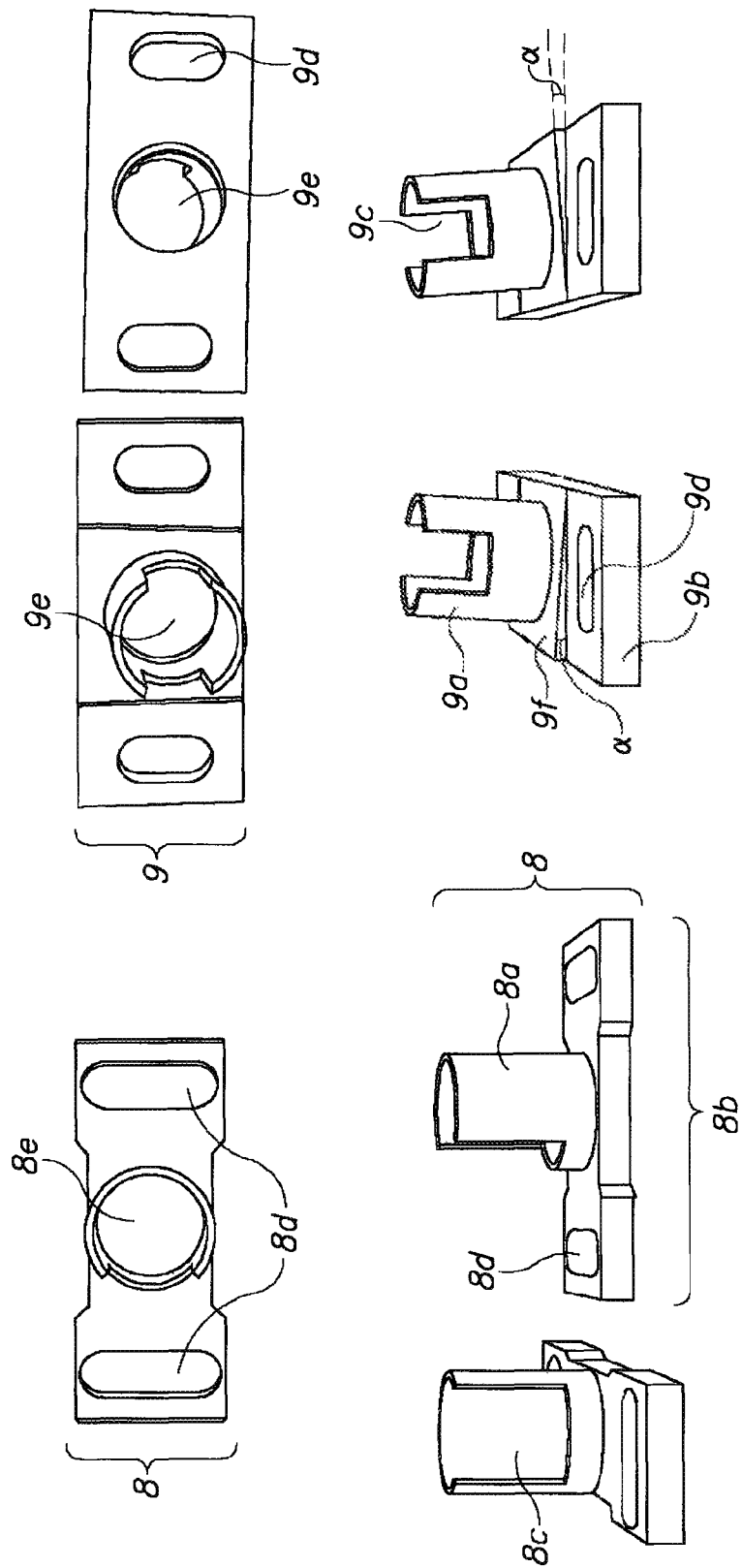

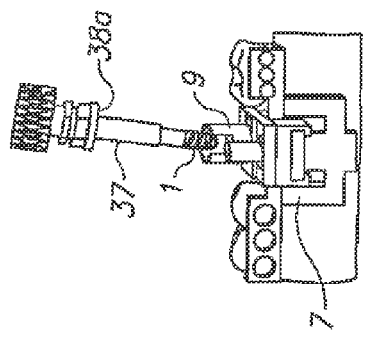
FIG.10A
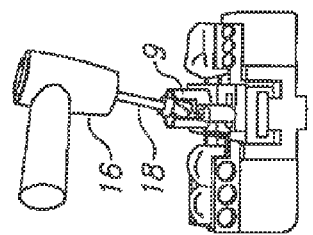
FIG.10B
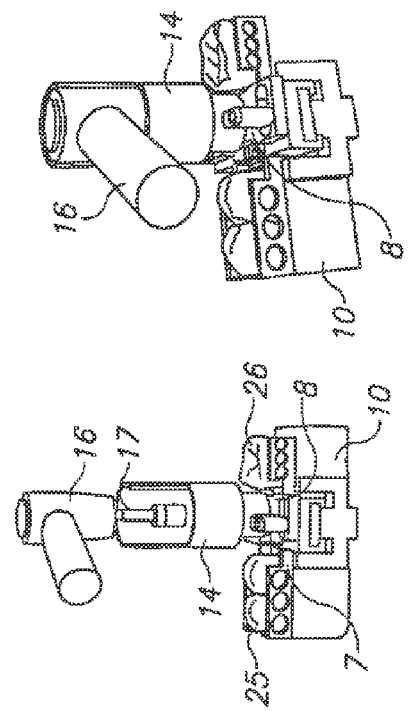
FIG.10C
FIG.10D
FIG.10E
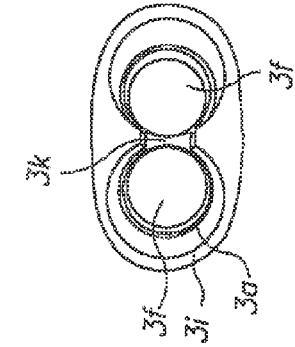
FIG.10F
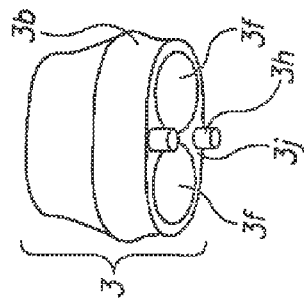
FIG.10G
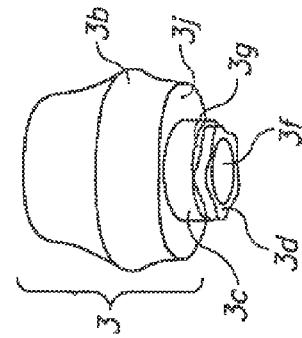
FIG.10H
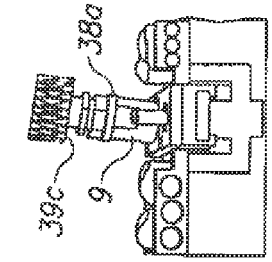

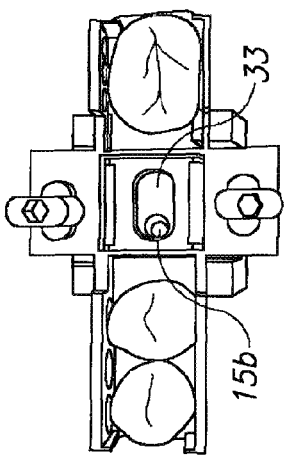
FIG.13A
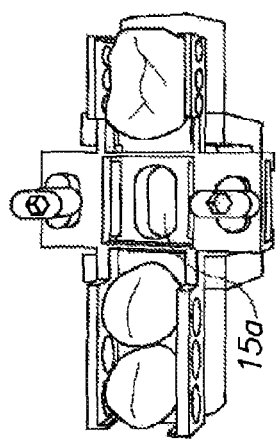
FIG.13B
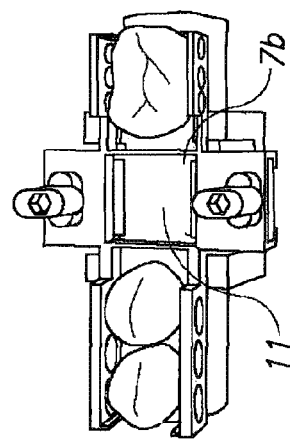
FIG.13C
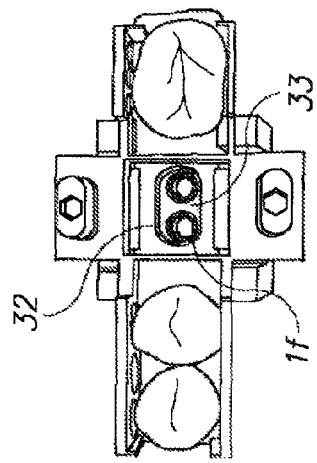
FIG.13D
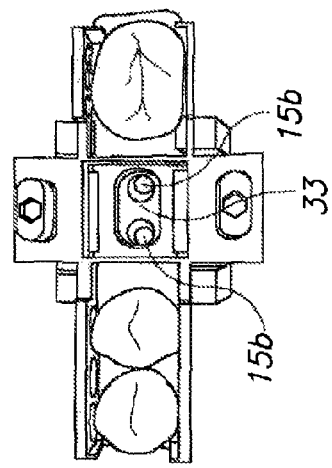
FIG.13E
FIG.13F

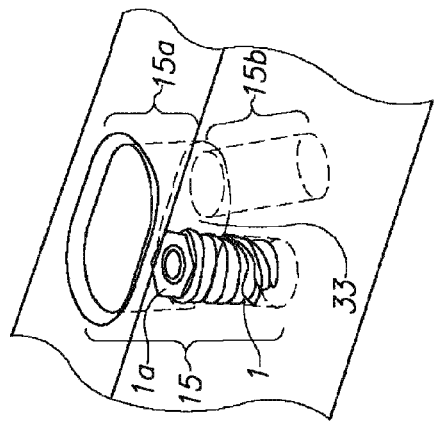
FIG.14L
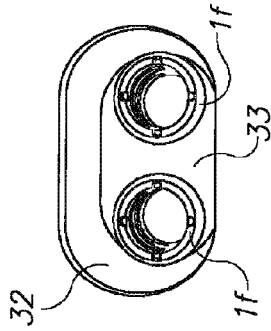
FIG.14M
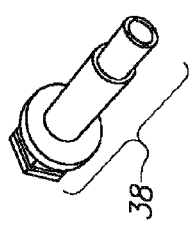
FIG.14H
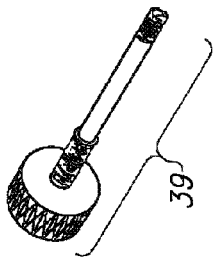
FIG.14I
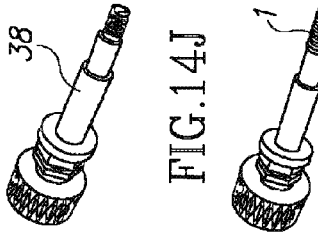
FIG.14J
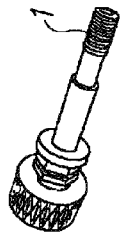
FIG.14K
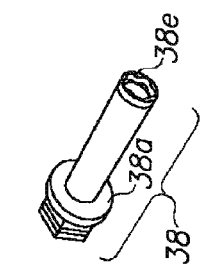
FIG.14D
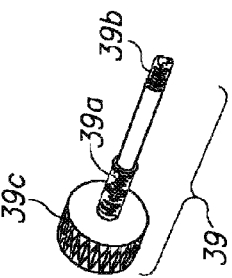
FIG.14E
FIG.14F
FIG.14G
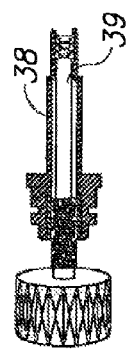
FIG.14A
FIG.14B
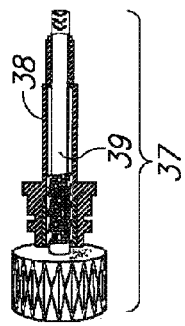
FIG.14C

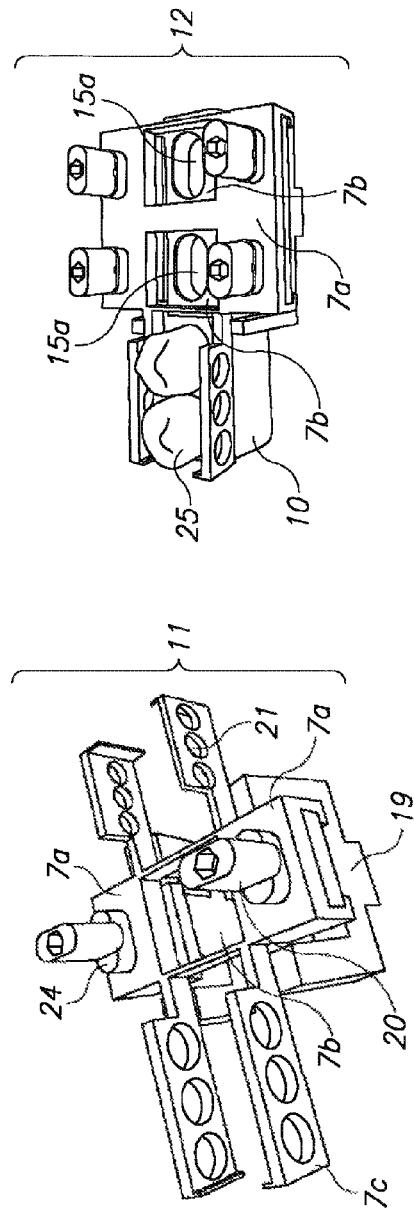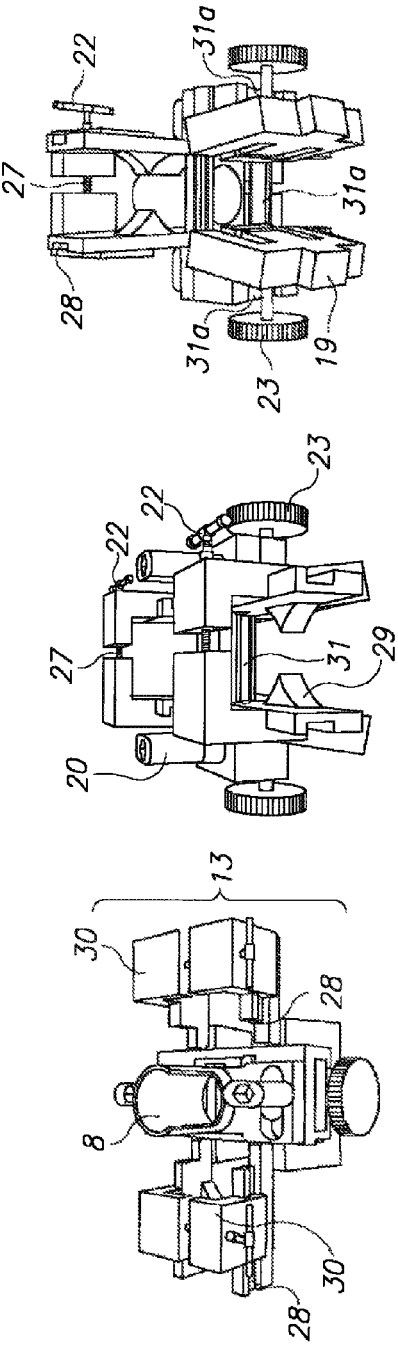

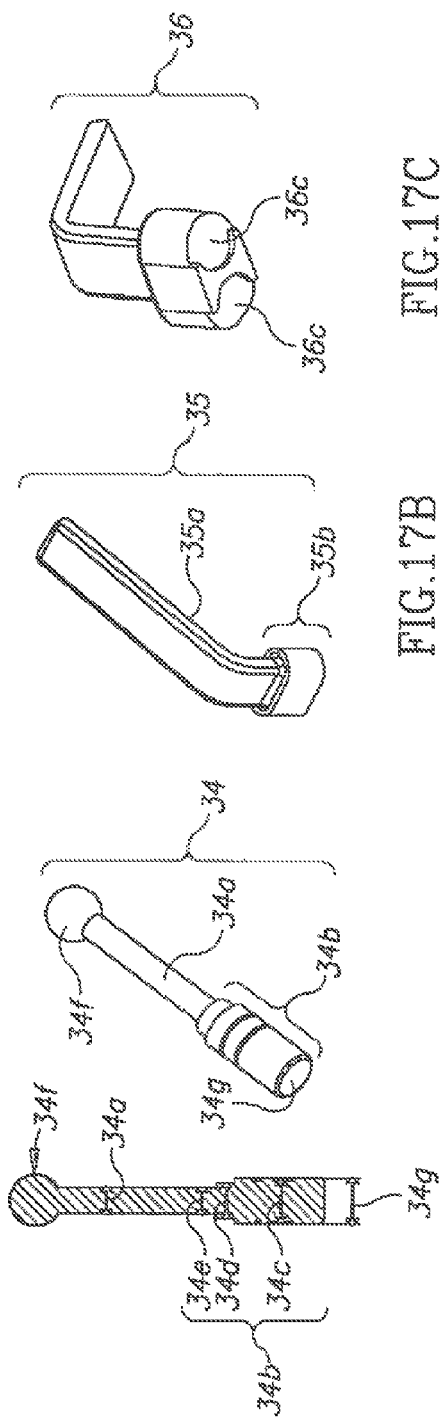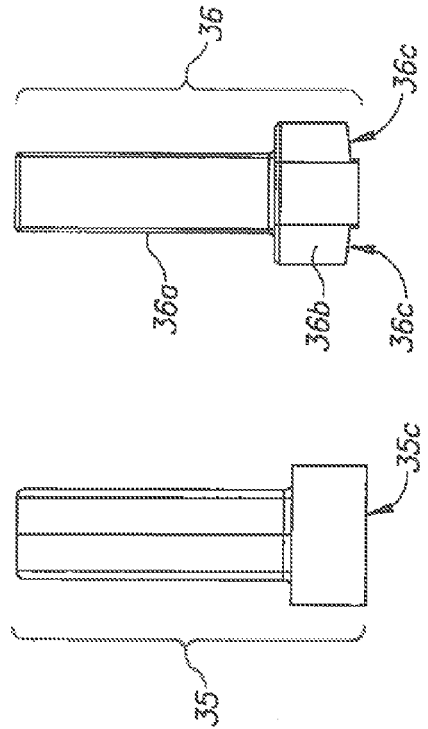

SYSTEM, APPARATUS AND METHOD FOR IMPLEMENTING IMPLANTS

CLAIM OF BENEFIT OF FILING DATE

The present application is a national phase filing under 35 USC §371 from PCT Patent Application Serial No. PCT/US2012/023436 (filed Feb. 1, 2012) (Published as WO 2012/106397 A1) and claims priority therefrom. This application further claims priority from U.S. Provisional Patent Applications 61/438,681 (filed Feb. 2, 2011) which is incorporated herein in its entirety by reference.

FIELD OF THE INVENTION

The present invention relates generally to bone implants, apparatus for implanting a bone implant, and methods for securing an implant to a bone. The bone implant may be an improved dental implant. The apparatus and method may be employed for preparing a bone and/or securing a dental implant into a bone, such as for a dental prosthesis for one or missing teeth.

BACKGROUND OF THE INVENTION

A dental implant is an artificial prosthesis normally comprised of a single cylindrical component to replace the missing root structure of a natural tooth that has been lost. This single stage is inserted into a prepared hollowed out bone preparation (osteotomy) in the patient's jawbone (endosseous) and typically remains buried there for a period of time to allow for "osseo-integration" or the growth and adhesion of natural bone around the implant "root screw", securing it in place. This cylindrical implant typically contains down its internal center a machined threaded internal hollow bore that allows the dental practitioner upon later surgical exposure of the head or top section of the cylindrical implant to screw into place a machined screw-in abutment (either with an integral screw on its inferior aspect or a separate connector screw which threads through a center hollow sleeve of the abutment). The head section of the implant is simply the top segment of the cylindrical implant form and is an integral part of it. The abutment, which extends into the oral cavity, is then utilized by the dentist to fabricate a single fixed prosthesis (crown).

There are several major drawbacks to this standard implant design. These drawbacks are derived from the fact that the standard implant design form is actually in very significant variance to the natural structural form of the roots of human teeth. There are different types of teeth in the humans, namely, the upper and lower incisors, canines (cuspids), premolars, and molars. These teeth differ to a significant degree in form from each other between the different categories, and they differ as well within each category depending on whether they are in the upper or lower jaws and which position they have in each jaw. These differences in form (and structure) apply not only to what is termed in dentistry as the crown portion of the teeth (the part of the tooth that is erupted into the mouth and visible to the eye) but extends as well to the forms of the root (s) portion (buried in the alveolar bone socket of the jaws) of these different categories of teeth in both the maxilla and mandible.

The mesial aspects (part of the root structure that is deep in the bone) of the natural roots of teeth are basically cylindrical or somewhat oval in cross-section. When one though observes in cross-section the natural form of the roots of teeth at the level of the transition of the tooth from its root segment to its crown segment (known as the root trunk) at the crest of the jawbones (this level is referred to in dentistry as the CEJ—cemento-enamel junction or the cervix of the tooth) one is immediately struck by the fact that in general most of the root forms of the root trunks in cross-section of the teeth are anything but cylindrical in shape or form (the standard dental implant form is cylindrical in cross-section along its entire length). Depending on the type of tooth in question, the natural root trunk form of the teeth in cross-section are in fact very oval at this level (at the cervix), either in a horizontal axis in relation to the crestal bone ridge of the jaw when one is referring to incisors, or oval in a vertical axis in relation to the crestal ridge when one is referring to the premolars, and quite rhomboid, oval or kidney shaped when one is referring to the molars. In addition, when one is referring to the molars, the natural teeth typically exhibit multiple roots (typically the molars are bi-rooted in the mandible and tri-rooted in the maxilla).

The standard dental implant design (endosseous) being cylindrical in form along its entire length including the head or top segment of the implant, and consisting of a very limited number of different sized single "root screw" cylinders takes none of the above mentioned natural variation of the roots of the different types of teeth (particularly the back teeth-molars) into account, both in the maxilla and the mandible.

Due to its cylindrical form along its entire length, the standard dental implant does not conform at the level of the crest of jawbone (level of the root trunk) to the natural oval, rhomboid or kidney-shape form of the roots of the natural teeth which sit in the bone (the head or coronal section of the standard implant is cylindrical in cross-section as well). This major discrepancy in the contour or emergence profile, as it is termed in dentistry, of the crown that is fixed upon the implant abutment (which of necessity must fit precisely into the head portion of the implant) in relation to the gums (as compared to the emergence profile of the natural crown of a tooth as it emerges from the natural root trunk of the tooth) results in large gaps or spaces between the implant crown and the teeth on either side of it and prevents the optimal formation of the interdental papilla (gum tissue between the teeth). With the posterior implant, the situation is very much analogous to a large ball sitting on top of a thin stick, where the ball is the crown and the standard implant is the stick. These large open areas or gaps allow for food debris, plaque, and pathogenic bacteria to accumulate between the implant crown and the natural teeth adjacent to it, making these areas very difficult for the patient to keep clean and requiring the patient to use special cleaning implements to try and maintain them free of food debris and plaque. In many cases this situation over the long-term results in poor health of the gums, causing periodontal (gum) disease of the adjacent teeth as well as documented cases of implant failure due to crestal bone resorbtion.

Additionally, as was previously mentioned, standard implants on the market consist of a single cylindrical "root screw" form or stage that is buried into the alveolus (jawbone) to replace the natural root of the missing teeth. A second stage abutment is later screwed into the "root screw" (the abutment sits above the bone in the mouth) and a crown is made to sit on top of the abutment. This represents your typical standard two stage implant (the crown is never considered as a stage of the implant. This accords to a relatively good degree for the replacement of all the missing anterior teeth in the mouth but is not at all in accord with the natural state for replacing the missing posterior teeth, where as was previously mentioned, the upper molars are typically tri-rooted and the lower molars are typically bi-rooted.

The upper and lower jaws are made up of a narrow strip of softer, spongy, alveolar bone sandwiched between two thin outer harder cortical plates of bone. In the posterior regions the entire width of the jawbones is typically only 5 to 7 millimeters thick. The average interdental (anterior-posterior length between the teeth) space remaining when a molar tooth is lost is 10 to 12 millimeters long. The vertical depth of alveolar bone present where the tooth was lost can be as little as 5 to 10 millimeters before one encounters either the maxillary sinus space (in the upper jaw) and the inferior alveolar nerve (in the lower jaw).

To allow for a proper volume or thickness of jaw bone between the implant and the adjacent teeth so as to allow for a proper blood supply and health of the bone between the implant and the adjacent teeth, it has been accepted in the dental field to maintain a minimum distance of 2 millimeters between the implant and the adjacent teeth on either side of the implant. As noted above, this means that the head (top portion) of the implant at the height of the crestal bone should not typically exceed a diameter of 6 to 8 millimeters in a mesio-distal dimension (the distance between the adjacent teeth where the missing tooth used to be), based on the formula: interdental space (space left by the missing tooth) minus 4 millimeters (2 millimeters on each side of the implant)=maximum diameter of implant head. In the particular case of the posterior teeth (molars) it is typically either 10−4=6, or 12−4=8. As mentioned above, the entire width of the jawbones is typically between 5 to 7 millimeters thick (referred to in the dental field as its Bucco-Lingual dimension) in the posterior area. This means that in order to stay within the confines of the jawbone and not puncture the outer cortical plates of the jawbone, the maximum dimension of the head of a standard implant which is round in cross-section should typically not exceed 6 millimeters in diameter.

This means that the target bone site for a dental implant is very limited and requires the practitioner who wishes to place dental implants to have acquired a high degree of skill level and clinical experience.

Dental implants are typically placed using the following two surgical techniques: 1. Delayed Implant technique: the unsalvageable tooth is extracted and the entire root socket(s) are allowed to heal with bone filling the void(s) over several months. Once this healing process has been completed, the practitioner opens the gum and drills into the bone to create the osteotomy (bone preparation) to allow for the insertion of the dental implant. 2. Immediate Extraction-Immediate Implant technique: At the same visit, or within a period of 4 weeks or fewer, the practitioner extracts the unsalvageable tooth and immediately inserts the dental implant into the root socket voids or using a drill modifies this root socket or drills a new hole and places the implant into it. In the case of a molar tooth extraction the practitioner is left with multiple proximal root socket voids in the jawbone (where the multiple natural roots used to be) and an oval or rhomboid distal void (where the root trunk used to be). An implant designed to closely resemble this negative shape would be seen advantageous, as it would require minimal or no drilling of the fresh extraction site in order to placed said implant into it (minimizing pain for the patient) and significantly reduce the time required for bone healing of the implant site and time to functional loading since less bone needs to grow around the implant in order to adapt to it (when the patient could actually chew solid food on the implant supported crown). However, until the present teachings, there has been a reluctance to pursue such an approach because of the limited implant designs available to the surgeon.

In an attempt to provide for a multi-rooted tooth form implant, WO Pat. App. No. 2006/082610 Aug. 2006, Cito. D'Ambrosio and Vinci, describes a "multiple-root" form dental implant design with a "head" component which it calls a "collar" and a "root screw" component which it calls a "fixture". For the sake of clarity the terms "head component" and "root screw" or alternatively "bone attachment" component used by the present teachings for these components will be used to describe these same respective implant components.

Another multi-root implant form design to the above described application is described in U.S. Pat. No. 2003/0180686, September 2003, Simmons.

Both of these applications describe a design wherein the "root screw" components are by necessity of smaller diameter or girth than the bore holes of the "head" component as their entire length (except for the limiting head) need to be inserted through these bore holes so that their wider diameter head can rest on the inner surface of the circumferential lip of the bore hole (which acts as a limiting stop) in order to relate these two components to each other.

This is a significant drawback in the structural design of both these applications for the following reasons: As noted above, there are significant limitations on the maximum interdental (mesio-distal distance between the teeth) and bucco-lingual (width of the jawbone) dimensions of the implant site. The diameter of the "head component" that can typically be accommodated in this limited implant site for missing molar teeth without puncturing this three-dimensional volume of the bone in both of the above two dimensions is itself quite limited. Therefore, the diameter of the bore holes contained within said head component must of necessity be of smaller diameter than the head component which contains them.

Both applications described above do not allow for the tight securing to each other of their head component and their root screw component at the time of initial insertion of these implant components into the fresh osteotomy of the jawbones (initial implantation). This is a significant drawback as it allows for potential micro-infiltration of pathogenic bacteria (at the time of initial implant surgery when the jawbone is directly exposed to the bacteria-laden oral environment as well as during the early stages of healing of the fresh osteotomy) into the micro-gaps between these unsecured endosseous (in bone) implant components and the creation of a reservoir of these pathogenic bone-resorbing bacteria between them. Additionally, as these endosseous (in the bone) implant components (the head and root screw components) are not tightly secured to each other, these components are free to shift their positions relative to each other during the several months that is required for the bone remodeling that occurs as part of the natural healing process of the osteotomy (implant preparation in the jawbone), another major drawback.

The above elements described may be critical requirements, as noted above, for the successful implantation of any dental implant and actually may be more critical requirements for the successful placement by the dental practitioner and long term viability of a "multi-rooted" posterior (molar) dental implant due to the larger number of components (compared to a "single-rooted" anterior implant) which must accurately be related to each other and related to the bone preparation fashioned to receive them. Additionally, a posterior molar implant should be able to handle the significantly greater amount of load (stress forces) it must withstand (typically 500 Newtons of force compared to 200 Newtons of force for the anterior teeth) due to its position and normal function requirements (holding up the bite and chewing forces) therefore the dimensional size of these implant components and their ability to withstand these significant force loads over decades is critical to the long term success or failure of these implant components and the assembled implant in its entirety.

SUMMARY OF THE INVENTION

One aspect of the present teachings is directed at a bone implant comprising one or more bone attachment components for securing the implant to a bone, and a head component independent of and separable from the bone attachment components. Each bone attachment component has a longitudinal axis. Preferably each bone attachment component includes an internally threaded bore hole for receiving a connector component. The head component preferably is adapted so as to be secured to the one or more bone attachment components at the time of initial implantation (e.g., during the same visit) of the bone attachment components and the head component into the bone (e.g., substantially, or even entirely endosseously). The head component preferably is adapted to be oriented relative to at least one of the one or more bone attachment components at a predetermined tilt angle between 0 and 90° relative to the bone attachment component, so that the implant generally conforms with a natural root structure of a missing tooth (e.g., as defined by an extraction cavity of a patient), wherein the tilt angle defined by the acute angle between the longitudinal axis of the bone attachment component and the longitudinal axis of the head component. The longitudinal axis of the head component may be in the generally apical-coronal direction.

This aspect of the present teachings may be characterized by one or any combination of the following features: the bone implant is a dental implant; the tilt angle is at least about 1°; the bone implant comprises two or more bone attachment components including two bone attachment components having longitudinal axis that are not parallel; the bone attachment components are root screws; the implant includes a first connector component; the first connector component is a screw; the head component includes a bore shaft having a first section that is angled relative to a second section of the bore shaft; or the implant includes an abutment component.

Another aspect of the present teachings is directed at a bone implant comprising a bone attachment component for securing the implant into a bone, a head component independent of and separable from the bone attachment component, wherein the head component is adapted to be secured in the bone (e.g., substantially, or even entirely endosseously) to the bone attachment component at the time of the initial implantation of the bone implant; and a first connector component that temporarily secures the head component to the bone attachment component at the time of initial implantation of the bone attachment component and the head component in a bone. The head component is also adapted to be secured to an abutment component at a later time. Preferably, each bone attachment component includes an internally threaded bore hole for receiving a connector component. The head component generally includes one bore hole per bone attachment component. Preferably, each bore hole of the head component has a limiting seat circumferential flange for receiving one of the first connector components. Each first connector component preferably has a distal head section that substantially fills the distal region of a bore hole of the head component. The first connector component preferably is removable so that it may be replaced by a second connector component that is sufficiently long for securing an abutment component that is distally positioned to the bone attachment component with the head component generally interposed between the abutment component and the bone attachment component. A further aspect of the present teachings is directed at a method for implanting a bone implant comprising the sequential steps of milling a recess in a bone, wherein the recess has a generally flat floor; drilling one or more bore holes in the bone through the floor of the recess, including at least one bone bore hole that is tilted at a predetermined tilt angle relative to the normal direction of the floor; inserting a bone attachment component in each bone bore hole through the floor, inserting a head component into the cavity of the first bone preparation and placing it over the distal ends of the bone attachment components; and securing the head component to a bone attachment component using a connecting component. Preferably, the predetermined tilt angle of at least one bore hole through the floor of the recess is about 1 or more. The process preferably is employed to install a bone implant having one or more of the features described herein. The process preferably employs a bone installing apparatus having one or more of the features described herein.

Another process related aspect of the present teachings is directed at a process for implanting a bone implant comprising the steps of: securing a surgical jig having a drilling platform to a patient jawbone; attaching and securing a removable sliding first drill guide assembly to said jig wherein said drill guide assembly is adapted to enable a controlled milling procedure in the jawbone of a symmetrical or asymmetrical bone preparation; performing a milling procedure to prepare a first bone preparation with a predetermined cross-sectional shape and uniform depth, using a hand piece guide sleeve adapter containing the drill head and attached milling drill bit which relates to the first drill guide assembly; and performing a guided drilling procedure to prepare a second bone preparation of one or more bore holes in the floor of the previously prepared first bone preparation, using a second drill guide assembly to which is related the hand piece guide sleeve adapter containing the drill head and attached bore drill bit. The guide sleeve preferably has a cut-out slot adapted to be attached and removed from a drill head. Such a guide sleeve may include a separate hole cut into the guide sleeve to allow for the unimpeded spray of irrigating solution from the drill head when drilling into a hard tissue. The process preferably is employed to install a bone implant having one or more of the features described herein. The process preferably employs a bone installing apparatus having one or more of the features described herein.

Alternatively, the surgical jig described above may incorporate a drilling platform which allows for the securing of multiple drill guide assemblies and the subsequent preparation of multiple implant bone preparations and or the insertion and securing of multiple implants into said multiple implant bone preparations or alternatively their insertion and securing in multiple natural extraction sockets that remain after the prior extraction of these teeth.

Another method related aspect of the present teachings is directed at a method of securing an implant comprising a step of replacing a first connector component that connects a head component and a bone attachment component with a second connector component adapted to secure an abutment component to the head component and to the bone attachment component, wherein the step of replacing is following osseointegration of the bone attachment component, the head component or both.

Yet another aspect of the present teachings is directed at an apparatus for the guided installing of a bone implant, such as a dental implant. The same apparatus used to prepare the osteotomy can also be used to install the endosseous implant components in a guided and controlled manner. Utilizing the second drill guide assembly which has been secured to the surgical jig, a driver tool, to which has been securely attached a root screw, is adapted to slide into the guide ring of the drill guide assembly at the same location and angle as the guide tube so as to screw the root screw into the previously prepared bone bore shafts or alternatively the natural root socket of a recently extracted tooth. The driver tool has a limiting collar that engages the guide ring of the second drill guide assembly, and so controls the maximum depth the root screw can be driven down into the bone bore hole or alternatively, the natural root socket void.

Yet another aspect of the present teachings is directed at tools which act as templates to check the accurate preparation of the osteotomy or to check the accurate insertion of the root screw(s) into the previously prepared bone bore hole(s) or alternatively, the natural extraction root sockets of a recently missing tooth.

The implants, methods, and apparatus of teachings herein may include one or any combination of the following: a head component having a limiting flange in (e.g., each of) its bore holes that allows for the tight securing of the bone attachment components (e.g., root screw(s)) to the head component in the bone at the time of initial implanting; a head component that allows for an angled relation and/or angled securing of the head component to one or more bone attachment components (preferably multiple root screws), such as with angled connector components, so that the assembled bone attachment component and head component is an analog of the entire natural root structure (e.g., implant parts generally match the extraction sockets of a recently extracted tooth with minimal drilling and minimal need for bone regrowth (e.g., no drilling and no need for bone regrowth); a ball and socket coupling of the neck of the bone attachment component and the head component so that a generally tight fit with substantially no micro-gaps can be obtained (e.g., thus allowing for greater tolerances in the preparation of an implant site); an implant that does not have an angled relationship between the head component and the root screw component wherein the implant includes a temporary first connector component that protects a bore hole of the head component (e.g., the first connector component may act as a cover screw to secure the head component to the root screw at the time of an initial implantation; a bone attachment component (e.g., a root screw) that is headless and that can be related (e.g., tightly related) to the head component and whose body diameter is larger than the smallest diameter of the bore hole of the head component; the bone attachment component has a generally convex neck or convex neck collar; the bone attachment component has a locking feature, such as a petal-shaped external locking feature (e.g., on its neck) that corresponds to a similar matching feature in the head component (e.g., in a bore hole of a head component); an apparatus for installing an implant that includes a surgical jig having novel clamping features according to the teachings herein; a novel first drill guide and/or second drill guide according to the teachings herein; a apparatus and methods for a novel milling procedure according to the teachings herein; novel apparatus and methods for drilling an angled bone bore hole; template(s) and methods for employing template(s) for checking and/or evaluating a bone preparation; a novel root screw driver according to the teachings herein; or a novel dental drill guide sleeve adapter for controlling and/or guiding a dental drill during one or more steps of a bone preparation.

A further aspect of the present teachings is directed at an implant kit including a plurality of head components including two or more (e.g., four or more, 6 or more, or even 10 or more) head components having different tilt angles so that a bone surgeon can choose an appropriate head component for an implant site. The implant kit preferably includes one or more bone attachment components, one or more first connector components, or any combination thereof.

While preferred that the teachings herein are of a type useful for Immediate Extraction-Immediate Implant techniques, they may also be employed for other implant techniques (e.g., Delayed Implant techniques).

Although the apparatus and methods described herein may be employed with the implants described herein, it will be appreciated that they may find utility for securing other implants, and particularly for securing dental implants.

The methods, apparatus, and implants, may find particular utility for implanting an implant in a bone having a cavity, such as a cavity from a missing tooth, without first re-growing bone in the region of the cavity. As such, a tooth may be extracted and an implant secured to a bone during the same procedure (e.g., with minimal or no bone preparation in order to allow for the insertion of the implant in to the extraction socket(s)), or shortly thereafter (e.g., within one, four, or 20 hours, within one three or five days, or within one, two, three, or four weeks). It will be appreciated that longer periods of time may be encountered between the formation of the cavity (e.g., of a missing tooth) and the securing of the implant. The various aspects of the invention allow for increased flexibility in the timing of the securing of an implant.

BRIEF DESCRIPTION OF THE DRAWINGS

The principles and operation of the system, apparatus, and method according to the present teachings may be better understood with reference to the drawings, and the following description, it being understood that these drawings are given for illustrative purposes only and are not meant to be limiting, wherein:

FIGS. 1*a* and 1*b* are illustrative cross-section profile sketches of root screw 1 designs showing features of the prior art.

FIG. 1*c* is an illustrative cross-section profile sketch of FIG. 1*b* (prior art) showing features of a root screw which has been modified.

FIG. 1*d* is an illustrative cross-section profile sketch of FIG. 1*c* (prior art) showing features of a root screw which has been further modified.

FIG. 1*e* is an illustrative cross-section profile sketch of the root screw 1 of the referenced prior art PCT/IB2010/050456 showing that the root screw has modified areas that remained from FIG. 1*c*.

FIG. 1*f* is an illustrative cross-section profile sketch of the root screw 1 of the referenced prior art PCT/IB2010/050456 of which the present invention is in part a derivative thereof.

FIG. 1*g* is an illustrative cross-section profile side by side comparison of the prior art root screw 43 profile and the profile 48 of the root screw 1 of the referenced prior art PCT/IB2010/050456 of which the present invention is in part a derivative thereof.

FIG. 2*a* is an illustrative cross-section profile sketch illustrating the prior art relation of the head component profile 49 to the root screw component profile 42.

FIG. 2*b* is an illustrative cross-section profile sketch illustrating another prior art relation of the head component profile 49 to the root screw component profile 43.

FIG. 2*c* is an illustrative cross-section profile sketch illustrating the relation of the head component profile 51 to the root screw component profile 48 of the referenced prior art PCT/IB2010/050456 of which the present invention is in part a derivative thereof.

FIG. 2d is an illustrative cross-section profile sketch illustrating the relation of the head component profile 51 to the root screw component profile 48 of the referenced prior art PCT/IB2010/050456 of which the present invention is in part a derivative thereof.

FIG. 4a is an illustrative length-wise cross-sectional view showing features of the prior art dental implant.

FIG. 4b is an illustrative length-wise cross-sectional view showing features of one embodiment of the dental implant of the prior art PCT/IB2010/050456 of which the present invention is in part a derivative thereof.

FIG. 4c is an illustrative length-wise cross-sectional view showing features of an improved implant according to the teachings herein, including features of the head component 2, the root screw 1, the temporary connector screw (surgical stage) 4a, and relational features of the components.

FIG. 4d is an illustrative length-wise cross-sectional view showing features of an improved implant according to the teachings herein, including the head component 2, the root screw 1, the abutment 3, and the final connector screw (prosthetic stage) 4b, and relational features of the components.

FIG. 5a is an illustrative length-wise cross-sectional view along the bucco-lingual (cheek to tongue) axis showing features of the endosseous (in bone) components of an improved dental implant according to the teachings herein.

FIG. 5b is an illustrative length-wise view along the mesio-distal (front to back) axis showing features of the endosseous components of an improved dental implant according to the teachings herein.

FIG. 5c is an illustrative length-wise view along the bucco-lingual (cheek to tongue) axis showing features of an improved dental implant according to the teachings herein.

FIG. 5d is an illustrative length-wise cross-sectional view along the mesio-distal (front to back) axis showing features of the endosseous components of an improved dental implant according to the teachings herein.

FIG. 5e is an illustrative length-wise cross-sectional view along the bucco-lingual (cheek to tongue) axis showing features of an improved entire dental implant 6 according to the teachings herein, including an abutment 3.

FIG. 5f is an illustrative length-wise view along the mesio-distal (front to back) axis of an improved entire dental implant 6 according to the teachings herein showing features of the implant and its components.

FIG. 5g is an illustrative length-wise view along the bucco-lingual (cheek to tongue) axis of an improved entire dental implant 6 including the abutment 3 having features according to the teachings herein.

FIG. 5h is an illustrative length-wise cross-sectional view along the mesio-distal (front to back) axis of an improved entire dental implant 6 having features according to the teachings herein.

FIG. 5i is an illustrative top view of an illustrative head component 2 showing features of the head component according to the teachings herein.

FIG. 6a is an illustrative cross-sectional view along the mesio-distal axis showing features of the prior art PCT/IB2010/050456.

FIG. 6b is an illustrative cross-sectional view along the mesio-distal axis of the head component 2 of an implant showing features of the head component according to the teachings herein.

FIG. 6c is an illustrative cross-sectional view along the mesio-distal axis of a head component 2 showing feature of the head component according to the teachings herein.

FIG. 7b is an illustrative side view of the root screw 1 of FIG. 7a and FIG. 7c is an illustrative top view of the root screw 1 of FIG. 7a.

FIG. 8a is an illustrative side view along the mesio-distal axis showing features of an improved entire dental implant 6 according to the teachings herein.

FIG. 8b is an illustrative see-through side view along the mesio-distal axis of an improved entire dental implant 6 according to the teachings herein.

FIG. 8c is an illustrative see-through side view along the mesio-distal axis of an improved entire dental implant 6 according to the teachings herein.

FIG. 9a illustrates three different views of a head component drill guide assembly 8 showing features of an apparatus according to the teachings herein.

FIG. 9b illustrates four different views of a bore shaft drill guide assembly 9 showing features of an apparatus according to the teachings herein.

FIG. 10a is an illustrative side view along the mesio-distal axis wherein is depicted a surgical jig 7 to which has been attached a head component drill guide assembly 8 and a dental handpiece 16 with a milling drill bit 17 inserted in it above a handpiece drill guide sleeve 14 showing features of an apparatus, method, and implant according to the teachings herein.

FIG. 10b is an illustrative side view along the mesio-distal axis wherein is depicted a surgical jig 7 to which has been attached a head component drill guide assembly 8 and a dental handpiece 16 fully inserted into a handpiece drill guide sleeve 14 showing features of an apparatus, method, and implant according to the teachings herein.

FIG. 10c is an illustrative side view along the mesio-distal axis wherein is depicted a surgical jig 7 to which has been attached a bore shaft drill guide assembly 9 and a dental handpiece 16 above it with a twist drill bit 18 inserted in it showing features according to the teachings herein.

FIG. 10d is an illustrative side view along the mesio-distal axis wherein is depicted a surgical jig 7 to which has been attached a bore shaft drill guide assembly 9 and a root screw driver 37 with an attached root screw 1 above the bore shaft drill guide 9 showing features according to the teachings herein.

FIG. 10e is an illustrative side view along the mesio-distal axis wherein is depicted a surgical jig 7 to which has been attached a bore shaft drill guide assembly 9 and a root screw driver 37 with an attached root screw 1 fully inserted into the bore shaft drill guide assembly 9 showing features of a method, apparatus, and implant according to the teachings herein.

FIG. 10*f* is an illustrative side/bottom view along the mesio-distal axis of an abutment 3 showing features of an abutment according to the teachings herein.

FIG. 10*g* is an illustrative side/bottom view along the mesio-distal axis of another abutment 3 showing features of an abutment according to the teachings herein.

FIG. 10*h* is an illustrative top view along the mesio-distal axis of an abutment 3 of FIG. 10*g*.

As illustrated in FIG. 11*f*, a bone implant including a head screw and one or more root screws may substantially fill or entirely fill an extraction socket 26*c*, such as the extraction socket of FIG. 11*e*.

FIG. 13*a* is an illustrative top view along the mesio-distal axis of a surgical jig 7 that may be used for an implantation process. As illustrated in FIG. 13*a*, the surgical jig 7 may be placed on a segment of a mandible 10.

FIG. 13*b* is an illustrative top view along the mesio-distal axis of a surgical jig 7 placed on a segment of the mandible 10, wherein is depicted a prepared distal upper portion 15*a*, such as for an osteotomy 15 having two or more stages.

FIG. 13*c* is an illustrative top view along the mesio-distal axis of a surgical jig 7 placed on a segment of the mandible 10 wherein is depicted a single bore shaft 15*b* prepared into the bony floor of the upper portion 15*a*, such as for an osteotomy 15 having two or more stages according to the teachings herein.

FIG. 13*d* is an illustrative top view along the mesio-distal axis of a surgical jig 7 placed on a segment of the mandible 10 wherein is depicted two bore shafts 15*b* prepared into the bony floor of the upper portion 15*a* of an osteotomy 15 (such as a two stage osteotomy) according to the teachings herein.

FIG. 13*e* is an illustrative top view along the mesio-distal axis of a surgical jig 7 placed on a segment of the mandible 10 wherein is depicted two root screws 1 screwed into two bore shafts 15*b* prepared into the bony floor 33 of an upper portion 15*a* of an osteotomy, such as the osteotomy 15 of FIG. 13*d*.

FIG. 13*f* is an illustrative top view along the mesio-distal axis of a surgical jig 7 placed on a segment of the mandible 10 wherein is depicted a head connector 2 inserted into the upper portion 15*a* of an osteotomy 15 and sitting (i.e., resting) directly on top of two root screws 1 previously screwed into bores shafts 15*b*, such as the root screws 1 screwed into the bores shafts 15*b* depicted in FIG. 13*e*.

FIG. 14*a* illustrates a lengthwise cross-sectional view of a body 38 of a root screw driver 37 according to the teachings herein.

FIG. 14*b* illustrates a lengthwise cross-sectional view of a body 38 of the root screw driver 37. The root screw driver 37 may have an inner adjustable screw 39 (i.e., internal adjustable screw) at least partially inserted into it.

FIG. 14*c* illustrates a lengthwise cross-sectional view of a body 38 of a root screw driver 37. The root screw driver 37 may have an inner adjustable screw 39 fully inserted into it.

FIG. 14*d* illustrates the lengthwise view of a different body 38 of a root screw driver 37.

FIG. 14*e* illustrates the lengthwise view of an inner adjustable screw 39 of a root screw driver 37.

FIG. 14*f* illustrates the lengthwise view of an inner adjustable screw 39 fully inserted into the body 38 of a root screw driver 37.

FIG. 14*g* illustrates the lengthwise view of an inner adjustable screw 39 fully inserted into the body 38 of a root screw driver 37 and to which has been attached a root screw 1.

FIG. 14*h* illustrates the lengthwise view of a body 38 of a root screw driver 37.

FIG. 14*i* illustrates the lengthwise view of another inner adjustable screw 39 of a root screw driver 37.

FIG. 14*j* illustrates the lengthwise view of an inner adjustable screw 39, such as the inner adjustable screw of FIG. 14*i*, fully inserted into the body 38 of a root screw driver 37.

FIG. 14k illustrates the lengthwise view of an inner adjustable screw 39, such as the inner adjustable screw of FIG. 14i, fully inserted into the body 38 of a root screw driver 37 and to which has been attached a root screw 1.

FIG. 14l is a close-up angled "see-through" view of an osteotomy 15 (e.g., a two-stage osteotomy) wherein the threaded body of one root screw component has been screwed down into one of the angled bore shafts and the top angled portion of the root screw is sitting in the empty void (above the floor) of the upper segment 15a of the osteotomy 15.

FIG. 14m is a close-up top view an osteotomy 15 with two root screws 1 fully screwed into bore shafts 15b. The distal (top) portions of the root screws 1 may sit above the bony floor 33 of the upper portion 15a of the osteotomy 15. Also depicted are the side walls 32 of the upper portion 15a of the osteotomy 15.

FIG. 15a is an illustrative top/side angled view along the mesio-distal axis of a surgical jig 7 showing features of a surgical jig according to the teachings herein.

FIG. 15b is an illustrative top/side angled view along the mesio-distal axis of another surgical jig 7 showing features of a surgical jig according to the teachings herein.

FIG. 15c is an illustrative top/side angled view along the mesio-distal axis of yet another surgical jig 7 showing features of a surgical jig according to the teachings herein.

FIG. 15d is an illustrative top/side view along the bucco-lingual axis of the surgical jig 7 of FIG. 15c.

FIG. 15e is an illustrative bottom view along the bucco-lingual axis of the surgical jig 7 of FIG. 15c.

FIG. 16b is an illustrative angled front view of the removable dental handpiece guide sleeve adaptor 14 of FIG. 16a.

FIG. 17a is an illustrative cross-sectional sketch of a bore shaft depth template 34 of the present invention.

FIG. 17b is an illustrative angled front view of a head component template 35 of the present invention.

FIG. 17c is an illustrative angled front view of a head component-root screw depth template 36 of the present invention.

FIG. 17d is an illustrative angled bottom view of a head component template 35, such as the template of FIG. 17b.

FIG. 17e is an illustrative cross-sectional sketch of a head component-root screw depth template 36, such as the template of FIG. 17c.

DETAILED DESCRIPTION OF THE INVENTION

Figure 3B:
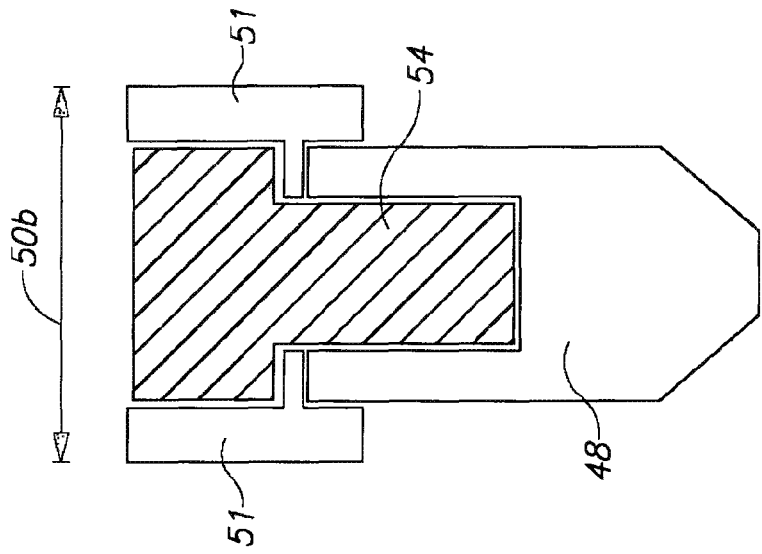
FIG. 3b is an illustrative cross-section profile sketch illustrating the relation between the head component profile 51, the root screw component profile 48 and the connector screw profile 54 that secures these two components to each other of the improved implant of the referenced prior art PCT/IB2010/050456 of which the present invention is in part a derivative thereof.

The following description is presented to enable one of ordinary skill in the art to make and use the teachings herein as provided in the context of a particular application and its requirements. Various modifications to the described aspects of the invention (including components, arrangement of components, apparatus, and methods) will be apparent to those with skill in the art, and the general principles defined herein may be applied to other aspects. Therefore, the present teachings are not intended to be limited to the particular aspects shown and described, but are to be accorded the widest scope consistent with the principles and novel features herein disclosed. In other instances, well known methods, procedures, and components have not been described in detail so as not to obscure the present teachings.

In general, the teachings contemplate systems, means and methods for the preparation and insertion of improved anatomically corrected implants that more closely imitate the overall natural form of the root system of human teeth. In some aspects of the present teachings, the system is an implant that includes two detachable modular stages with customizable features to which a third abutment stage is attached. The system may employ, e.g., as an integral part, one of the two stages as is described in PCT Patent Application PCT/IB2010/050456 (WO2010/089698 A2), by the same inventor, which is hereby incorporated in its entirety by reference.

Moreover, in accordance with various aspects of the present teachings, a modular design two stage multi-root endosseous dental implant system is provided, comprising multiple detachable and modular stages which are placed endosseously, including a first stage comprising one or more bone attachment components (e.g., multiple novel root screw components), a second stage comprising a head component (e.g., a novel head component according to the teachings herein), or both.

The head component and the abutment component may be configured as separate stages. The head component and the abutment component may be secured at different times.

The modular design dental implant system may include one or more bone attachment components (e.g. multiple cylindrical root screws). The bone attachment components may be placed endosseously. As such, the bone attachment component may provide a splinting effect when coupled with a second stage, such as a head component (i.e., a head component stage). The head component preferably includes side walls that generally conform at the level of the cervix to the natural root form of a selected tooth type.

As can be seen from the various embodiments described on the teachings herein, one of the novel aspects is predicated upon the surprising recognition of a unique head component structure and method of making and using the same pursuant to which it is possible to achieve (and preferably in which there is achieved) a secure attachment of one or more bone attachment structures (such as a root screw) that is implanted into a bone (e.g., a mandible) at the time of performing the initial implant procedure (and thereby potentially reducing patient visits, and simplifying overall implantation as compared with the previously described standard implant technology). For example, the employment of one or more limiting flange in a bore hole of the head component helps to assure a fastened assembly of the head component with a bone attachment component.

Further, as to one of the aspects of the teachings herein, by virtue of the employment of an angled relation and an angular securing of the head component to angled bone attachment structures with one or more fasteners such as angularly oriented screws an assembly is employed that more closely approximates that of an entire natural root structure. For example, it is seen from the teachings herein that the bone attachment component defines a unique structure that functions to interconnect a head component with bone (e.g., with the bone of a mandible, as placed within a root socket from an extracted tooth). In this manner, the ability to match implant components to extraction sockets of a recently extracted tooth is realized with minimal drilling and minimal need for bone regrowth; that is, as compared with a procedure in which a bone attachment component that substantially approximates a natural root structure of a tooth is not employed, a) it is possible to accomplish the implant with a reduction of at least 20%, 30%, 40%, or more bone removal via drilling; b) it is possible to reduce the amount of bone re-growth necessary for the implant by at least a 20%, 30%, 40% or more with a similar reduction in the need to place bone grafting material in the extraction sockets at the time of initial implantation in order to facilitate bone regrowth. Thus, again, the teachings herein contemplate extracting a tooth for forming an extraction socket, inserting the described bone attachment component into the extraction socket (optionally substantially contemporaneously with the time of the extraction, or within 2 weeks, 1 week, 5 days, 3 days, 2 days or one day of the extraction), and then attaching the head component in the extraction socket to the bone attachment component.

Another beneficial aspect of the teachings herein is realized from the surprising employment of a ball and socket coupling of the bone attachment component with the head component. In this manner it is possible to attain (and the teachings herein contemplate attaining) highly precise attachment of the components while realizing a substantial absence of any gap between the components. For example, it is contemplated that any gap between components is less than about 50 microns, less than about 10 microns, or smaller. At the same time, by virtue of the ball and socket, adjustments to position of the components relative to each other are possible in the event of tolerance differences of the component, implantation orientation imprecision, or both.

As to the bone attachment component herein, the structure may be headless; it may employ a generally convex neck and/or neck collar structure; it may have a body diameter that is larger than a bore hole defined in a head component to which it is attached via a fastener; it may have an external locking structure (e.g., a generally petal shaped external locking structure) that corresponds generally in shape with an opposing structure in the head component (e.g., a complementary shape for mating with a bore hole of the head component); or any combination of the foregoing.

The head component stage preferably includes one or more (e.g., multiple) connecting bore holes for the secure attachment of the first and second stages. The modular multi-stage dental implant preferably is adapted so that a separate abutment stage may be (and desirably is) secured to the separate head component stage, to the separate bone attachment component, or both. In various aspects of the invention the dimensions and/or placement directions of each of the bone attachment components (e.g., multiple root screws) is parallel or angled from each other, and/or may be attached in parallel and/or otherwise angled to the head component stage. The head component may include a sufficient number of micro-grooves and/or ridges on one or more external surfaces, so that retention and/or bone adhesion is enhanced. As used herein, micro-grooves desirably are a plurality of grooves having a spacing between successive groove bottoms of less than about 200 μm, preferably less than about 50 μm. Preferably, such grooves extends along the entire circumference of the head component.

Preferably, head component and the bone attachment component (e.g., the root screws) relate to each other passively in the following manner: the bottom (proximal) surface of the head component is placed (e.g., rests) on top of the top (distal) surface(s) of the bone attachment component. The distal surface of the bone attachment component may be the top surface of the neck of a root screw. This passive relation of these two implant components may be a flat butt joint. Alternatively, this passive relation may be a more intimate male-female interface. To secure head component and the bone attachment component to each other may require one or more connector components, such as a connector screw. For example, the connector screw may have a threaded length body section. The threaded length body section of the connector screw may slide partially or entirely through the bore hole of the head component and engage the internal threaded bore hole sleeve of the bone attachment component (e.g., root screw). The connector component may have a head (such as a screw head) that rests on a limiting flange (seat) of the internal bore hole(s) of the head component.

In order to achieve an angled relation of the bone attachment components(s) to the head component, a novel head component may be employed. The novel head component preferably incorporates one or more angled sockets (such as an indented set ring) on its bottom exterior surface which is related to the top (distal end) surface of a bone attachment component (e.g., a root screw). To allow the securing of this angled relation of these two components a lower section of a bore hole shaft of the head component may be angled in relation to an upper section of the bore hole shaft. The head component may also include a limiting flange in the lower section of the bore hole so that the head of the connector component (e.g., a connector screw) does not slide completely through the bore hole. If the head component is intended to be attached to a plurality of bone attachment components, then one, two or more (e.g., all) of the bore holes may have an angled lower section. These internal structural features of the novel head component of the present invention allow for the insertion and full seating of the connector screw(s) (e.g., first connector screws) through these internal bore hole shaft(s) at an angle that corresponds to the angle of the indented socket(s) (e.g., indented set ring(s)) on the bottom exterior surface of the head component, for the full seating of the screw head of the connector screw on the limiting flange, or both; so that the head component can be tightly secured to each of the bone attachment components at a predetermined tilt angle at the time of initial implantation of these components in the bone.

It will be appreciated that the teachings herein, in addressing "angularity" or "angled" relations or orientations envisions a positioning of two or more adjoining structures, each having a longitudinal axis, such that the longitudinal axes of the structures are not aligned or parallel with each other, For example, the axes may be oriented at an angle of greater than 0°, less than 180°, or both.

The tilt angle between the head component and bone attachment component is defined by an acute angle (and greater than 0°) between the longitudinal axis of the head component and the longitudinal axis of the bone attachment component. The tilt angle of each bone attachment component may be the same or different. The tilt angle of each bone attachment component may be determined by the selection of the head component. As such, the head component may be selected to provide tilt angles that will result in a bone implant that generally fills a cavity created by a missing tooth. When a plurality of bone attachment components are employed, a bone attachment component may have a longitudinal direction that is parallel with the longitudinal direction of the head component, particularly if the cavity created by a missing tooth includes a missing root section that extends nearly vertical in the apical direction.

The multiple internal bore hole shafts, the angled limiting seat flanges, and indented set rings on the bottom exterior surfaces of said novel head component can be manufactured at different angles and these angles can vary within the same head component for each bore hole shaft so that the root screws connected to said head component can be related and secured to each of these separate set rings at each of these different angles.

The described assembled implant of the present invention with a resultant orthogonal implant structure allows for mechanical stress breaker features between the attached separate components, thus reducing the mechanical stress on the entire implant structure.

In some embodiments, the internal bore hole shaft(s) of the novel head component are not uniform along their entire length in regard to their diameter and their angle. In some embodiments the upper section of these internal shafts have a larger diameter, are vertically straight, and incorporate threaded indentations to accommodate the insertion and securing of an abutment screw(s) (second connector) into this section of the internal bore hole shaft of the head component. The lower section of the internal bore hole shaft is angled in relation to this upper section and is of smaller diameter and may be unthreaded.

These two different sections of said internal bore hole shafts allow for the insertion of two separate and different diameter internal first and second connector screws. The upper section of the internal shaft accommodates the vertically straight insertion of a larger diameter abutment screw (second connector) and securing of the separate abutment component to the head component with a limiting circumferential seat for the screw head of said abutment screw incorporated in the screw bore hole of the abutment component. The lower section of the internal bore shaft accommodates the insertion of the smaller diameter connector screw(s) (first connector) in either a vertically straight (PCT/IB 2010/050456) or in the present invention at a vertically straight or an angled orientation. In some of the embodiments of the present invention, as was previously described, the connector screw(s) are inserted and seated in an angled orientation corresponding to the angled orientation of the lower segment of the internal bore hole shaft, and the inner surface limiting circumferential flange (seat) of the bore hole shaft of the novel head component is also angled to a corresponding degree to allow for the flush seating of the limiting wider diameter screw head of the connector screw(s) so as to properly secure the head component to the root screw(s) in a tight manner.

In one approach, a head component adapted to be attached to a bone attachment component at a predetermined tilt angle, may comprise a novel internal bore hole shaft including different sections having an angled arrangement. Preferably such a head component has a lower section of the internal bore hole shaft(s) that is angled in relation to the upper section of the internal bore hole shaft(s). For example, the lower section may be generally parallel with the longitudinal axis of a bone attachment component, the upper section may be generally parallel with the longitudinal axis of a head component, or preferably both. The internal bore hole shaft of the head component may contain an area on its internal aspect that is 1) not threaded, 2) angled in line with the angle of the lower section of the bore hole shaft, or preferably both, so that the lower section allows for an unimpeded angled path of insertion of a connector component (e.g., first connector), such as a connector screw. The connector component may be attached to (e.g., screwed into a threaded shaft of) a bone attachment component screw with a driver tool. The driver tool for the connector screw may be inserted at the same angle through the upper section of the internal bore hole shaft(s) of the head component and into the lower section.

A head component according to the teachings herein, such as a head component having an angled lower section of the internal bore hole shaft(s), may be adapted to contact, or mate, with a bone attachment component in a generally non-planar arrangement. The exterior surface of the bottom of the head component may have an angled surface (e.g., of the indented set rings) that is 1) asymmetrical shaped, 2) concave or convex in shape (e.g. spherically concave in shape) so that the top (distal) surface of the bone attachment component (e.g., a root screw component) may fit snugly against the bottom exterior surface of the head component set rings (e.g., in a ball and socket arrangement). Advantageously, such an arrangement may allow, in the case of slight inaccuracies of insertion (e.g., inaccuracies of the angle of insertion of the bone attachment components in the bone bore holes, or alternatively, in the natural root sockets of a recently missing tooth), the head component and the bone attachment component to relate to each other in an intimate manner (e.g., in the bone). Preferably the bottom of the exterior surface of the head component is concavely shaped (e.g., spherically concave in shape) and the distal surface of the bone attachment component is convexly shaped (e.g., spherically convex in shape), or vice versa.

Another aspect of the present teachings is directed at a head component having one or more features that allow for improved securing in a fresh osteotomy. This aspect of the invention may be combined with the other aspects of the teachings herein. Particular utility of this aspect of the invention is found in a head component which is connected to a single root screw, though the present teachings also apply to multiple root screws. The head component preferably has an internal bore hole shaft extending along the entire longitudinal axis of the head component that is free of internal threading, particularly in the distal region of the bore hole shaft (e.g., near the top of the bore hole shaft). The head component preferably includes a limiting circumferential flange in the internal bore hole shaft. The head component incorporates features, such as described above, which allows for the tight securing of the two endosseous (in bone) implant components (head component and bone attachment component) to each other at the time of initial insertion (e.g., during a surgical stage visitation) of these components into the fresh osteotomy or extraction site (initial implantation) with a first connector component (e.g., a temporary connector screw) having an externally threaded shaft that partially extends through the internal bore hole shaft of the head component and engages with an internally threaded bore hole on the distal end of the bone attachment component. When employed in securing the two components, the first connector component has a head (e.g. a limiting screw head) located in the internal bore hole shaft of the head component. Preferably the head of the connector component is generally flush with the top (distal) surface of the head component. The head of the connector component may be a screw head that compresses against the limiting circumferential flange of the internal bore hole shaft of the head component when the connector component engages with the bone attachment component. Preferably, the connector component is tightened to a predetermined torque range so that a sufficient compressive force is exerted between the head component and the bone attachment component. As such, the temporary connector component may secure the bone attachment component and the head components during healing of the implant site, may act as a cover screw to prevent bone from growing into the internal bore hole shaft of the head component, or preferably both. The temporary connector component may then be replaced at a later time, e.g. after full healing of the osteotomy has occurred. Preferably the temporary connector component is replaced with a final (e.g., prosthetic stage) connector component (e.g., a connector screw) which is of greater length and having a limiting head (e.g., limiting screw head) that fits into the limiting seat circumferential flange of the screw bore hole shaft of an abutment component, so as to secure the abutment component to both the bone attachment component and the head component.

The head component according to the teachings herein may optionally include one or more cut-out slots on its superior (top) surface and the abutment component may include one or more corresponding extensions on the bottom surface of the abutment component, or vice versa, to form one or more male-female interlocking features. Such male-female interlocking features may advantageously 1) allow for increased frictional fit between these two separate components, and 2) allow for ease of proper relating of these two components to each other by the operator.

The bone attachment component(s) (e.g., root screw(s)) according to the teachings herein, may have an internal threaded bore hole sleeve on its distal (top) surface that incorporate one or more cut out slots along its inner lip. Such cut out slots may advantageously allow for the insertion of a driver tool with corresponding extensions on its proximal lip for the secure screwing of the bone attachment component into the bone (e.g., jawbones).

The bone attachment component(s) (root screw(s)) according to the teachings herein, may have a distal portion that incorporates a neck (such as a generally cylindrical neck) having a smaller cross-sectional size (e.g., a smaller diameter) than the other regions (e.g., the rest) of the body of the bone attachment component. The neck may incorporate generally horizontally oriented flanges having a suitable shape so that they may act as a "locking" anti-rotational element. An illustrative flange that may be employed is a flange that is generally petal-shaped. Preferably, the flange prevents rotation between the head component and the bone attachment component when the neck inserts into a lower section of the bore hole of the head component. The neck may also incorporate a convex limiting seat collar. A petal-shape as used herein may refer to a form or shape having a plurality of lobes or other projection that generally radiate from a central region, and thus may be considered to resemble floral petals.

The head component according to the teachings herein may have an internal bore hole shaft that incorporates a horizontally oriented flange on the top (distal) segment of the internal bore shaft hole. The flange preferably has a suitable shape so the flange acts as a "locking" anti-rotational element. An illustrative flange that may be employed is a flange that is petal-shaped. The flange may allow for the insertion of a corresponding feature extending from a proximal ring of an abutment component in order to provide an anti-rotational "locking" element between the head component and the abutment component. A similar, or different element may be incorporated at the bottom (proximal) end of the internal bore hole shaft. Such an element (e.g., flange) may allow for the insertion of a corresponding feature of the distal (top) neck of the bone attachment component into the head component, as noted above, to again provide for an anti-rotational "locking" feature between these two separate components as well. The lower section of the internal bore hole shaft may also incorporate a concave limiting flange which would act as a limiting seat for the matching convex limiting seat collar of the neck of the root screw (e.g., a ball and socket arrangement) described above.

Precision bone preparation of a target bone site of the jawbone (osteotomy) for the improved implants, according to the teachings herein, is required to allow for the precision delivery of the implant into the bone preparation (osteotomy).

The precision delivery of the implant may employ a novel surgical guidance and delivery system. The guidance and delivery system may include one or more (e.g., a combination) of the following features:

A: A jig platform, such as a jig platform that sits generally on top of the crestal ridge of the jawbone. The jig platform may be reusable or may be a "single-use only" disposable or throw-away item, such as an item intended for a use in a single bone site preparation. The jig platform may be secured to the jaw by means of any variety of clamping elements. Suitable clamping elements may include elements that function by clamping to teeth in the mouth, bone screws that directly fix the jig platform to the jaw, or any combination of these two types of securing elements. The clamping elements may have clamping arms with retentive cut outs for the placement and hardening (e.g., by polymerization, crosslinking, or both) of a dental composite material as is commonly known in the art, or a bonding material, suitable for further securing the jig platform to the adjacent teeth and jawbone. The jig platform may include one or more cut outs through a surface (e.g., a top surface), where each cut out may be employed to allow access for an osteotomy. The jig platform may have one or more attachment points for positioning a drill guide assembly in a precise relation to the jig platform, to the osteotomy, or both. The jig platform may allow for the preparation of more than one osteotomy, such as by providing a platform with multiple cut outs through its top surface, by providing multiple attachment points for multiple drill guide assemblies on the same platform, or both. Such a jig platform may allow for multiple osteotomies to be prepared without moving the jig platform once it has been secured in one position to the jawbone. The jig platform may contain integrated pins and other structural features for the relating of other elements of the guidance and delivery system to it.

B. A head component drill guide assembly (first drill guide) that may include one or any combination of the following structural elements: 1. a tube or ring with a cut out slot (e.g., in its side) and a superior lip to said tube; 2. a relatively small platform (e.g., in relation to the size of the jig platform) perpendicular to the tube or ring to which the tube or ring is attached integrally attached; or 3. multiple (e.g., two) slotted tracks cut into the ring base to allow for the sliding of this part along a specified distance when this part is attached and secured to the jig platform.

C: A bore shaft drill guide assembly (second drill guide) comprising one or more (e.g., all) of the following structural elements: 1. a tube or ring with a cut out slot in its side and a superior lip to said tube or ring, where the tube or ring may be vertically straight or angled to various degrees to its ring base; or 2. a ring base with cut out slots or other cut out features and adjustable locking features for the temporary securing of the bore shaft drill guide to the jig platform and the ability to re-orient the bore shaft drill guide on the jig in order to prepare multiple bore shafts at different angles to each other in the same osteotomy (implant bone preparation).

D. External pins or other adjustable locking/unlocking features for further securing and removal of either the head component drill guide or bore shaft drill guide to the jig platform.

E. A removable handpiece adaptor drill guide sleeve for a dental handpiece (i.e., a dental drill). The drill guide sleeve may be a dip-on component. The drill guide sleeve may be disposable or may be suitable for repeated use. The jig adaptor drill guide sleeve may be shaped to intimately fit onto the head section of a dental handpiece, such as a dental handpiece according to the teachings herein. The drill guide sleeve may be formed to intimately wrap-around the head of a dental handpiece. The jig adaptor drill guide sleeve may include a slot cut into its side for the lateral insertion of the dental handpiece head, and a cut-out hole that allows for the unimpeded release of irrigant from a dental handpiece head to spray onto a target bone site (e.g., providing an unobstructed direct spray flow path), or both. The drill guide sleeve may be used as an adaptor to guide the dental handpiece onto the head component drill guide or the bore shaft drill guide (e.g., for drilling the bone void for the head component or a straight or angled bore shaft) so that it provides an operator accurate and/or precise control of the bone drilling process to prepare two stages (head component bone preparation and bone attachment component bore shaft bone preparation(s)) of the osteotomy.

F. A head component preparation check template suitable for checking one or more features of the head component preparation. This template may have a handle attached to a section shaped to one or more dimensions of the head component. The handle may be straight or angled. When inserted into the head component preparation segment of the osteotomy, this template may be capable of checking one or more dimensions (e.g., a depth, a length, a width, or any combination thereof) of the preparation, checking an overall shape of the preparation, checking smoothness and/or flatness of the floor of the preparation, or any combinations thereof.

G. A bore shaft depth check template suitable for checking one or more features of a bone bore hole. The bore shaft depth check template may have a handle attached to a cylindrical solid notched shaft. The handle may be a straight or angled handle. The notches may correspond to different depths (e.g., in spaced increments such as in millimeters). The template may be used to, check the depth of the bore shaft(s) that were drilled into the target bone site.

H. A bone attachment component depth check template (e.g., a root screw depth check template) suitable for checking one or more features of a bone attachment component having been inserted into a bone bore shaft of the preparation. This template may have a handle attached to a section shaped to one or more (e.g., all) of the dimensions of the head component with either straight or angled cut-outs on its bottom surface. The cut-out areas preferably fit over the top the surface of one or more bone attachment components (e.g., root screws) after they have been inserted (e.g., screwed) into the prepared bore shafts of the osteotomy. The handle may be straight or angled. This template may be used to check if the bone attachment component(s) have been inserted into these bore shafts to the proper depth, to check whether the bone attachment components are generally level with each other, or both.

I. A root screw driver. A particularly useful root screw driver is a novel root screw driver that has a separate inner adjustable screw which is inserted into the driver and can be turned to engage the internal threaded bore hole sleeve of the bone attachment component, to disengage the internal threaded bore hole sleeve of the bone attachment component, or both, in addition to other engaging elements of the root screw driver. The inner adjustable screw allows for the disengaging of the driver tool to the root screw without unthreading the root screw from its inserted position in the bone bore shaft, or alternatively, the natural root socket of a recently extracted tooth.

As mentioned above in the referenced PCT Patent Application No. PCT/IB2010/050456, which is fully incorporated herein by reference, the head component and the bone attachment component(s) relate to each other passively in the following manner: the bottom (proximal) surface of the head component is placed on top of the top (distal) surface(s) of the neck of the bone attachment components(s). This passive relation of these two implant parts can either be a flat butt joint or a more intimate male-female interface (indented set ring(s) on the exterior under-surface of the head component). To secure these to each other requires a connector component(s) (e.g., connector screw(s)) whose threaded section slides through the internal bore hole shafts of the head component and engages the internal threaded bore hole sleeve of the bone attachment components and whose head (of the connector component) rests on the limiting flange of the connector internal bore shaft hole(s) of the head component.

The above novel design of the head component (to be described in detail below) and its relation to the bone attachment component(s) of the improved implant of the present teachings may have beneficial (benefits, including:

1. the design shape of the root screw utilized in the present invention as compared to the previously listed applications;
2. the angle or angles at which each bone attachment component is related and secured to the head component;
3. the long-term durability and success of the improved implant of the present invention as compared to the prior applications, or any combination thereof.

In the above described applications to those other than the inventor herein, the relations of implant components typically involve employing a limiting head to the root screw with a larger diameter than its body in order to create a limiting seating step to said root screw component so that the head of the root screw component(s) can rest on the inner surface of the limiting seating flange of the head component and not fall through the internal bore hole. In various aspects of the present invention (as was seen in PCT/IB2010/050456) no additional wider diameter head of the bone attachment component is needed as the root screw (e.g., in embodiments it is contemplated that the bone attachment component may be headless) is not inserted through the internal bore hole of the head component in order to relate it to the head component.

In all the prior applications described above, the diameter of the entire body of the root screw component(s) must be smaller than the diameter of the internal bore hole of the head component so that it can slide through the bore hole. This limiting factor can potentially be of critical importance when evaluating the long term durability, viability and clinical success of the applications described above as compared to the improved implant of the present invention.

The prior art design, by incorporating in a basic design a "root screw" that must of necessity be of smaller diameter than the internal bore hole of the "head" component into which it slides through, requires the "root screw" component of the applications described above to be extremely narrow in its exterior diameter, resulting in what may become an insufficient structural diameter or girth of these "root screw" components. The inadequate diameter and resulting inadequate structure of these "root screws" may potentially be even more problematic when one considers the fact that most "root screw(s)" in general do not have a solid core and in fact must contain an internal hollow bore hole shaft to accommodate the connector screw which threads into it. This means that the resultant structural thickness of the outer walls of the "root screw" design of the applications described above must be extremely thin and would be very prone to fracture (resulting in complete failure of the implant) under even a minimal load. The present invention contemplates that an exterior diameter root screw that is broader than the connector screw may be employed (in contrast to that of the prior art), and due to the overall structural differences, problems faced by the prior art designs can generally be avoided.

Additionally, the very small diameter of the "root screw" components necessitated by the design of the prior art also necessitates that the single set of "connector screws" (first connectors) provided by these applications to secure all three components (the "head", "root screw" and abutment components) to each other to be even structurally thinner than the "root screws" (as they must thread inside them), which, over time, (or even under initial load) potentially could lead to their fracture under load. This would cause a separation of all three implant components and a separation of the two endosseous (in bone) components (the head component and the root screw) within the jawbone.

Additionally, the abutment stage design of some of the prior art applications describes projecting tubes on the bottom surface of the abutment which extend through the internal bore holes in the head component in order to relate these components to each other. This design feature as specifically described in the context overall of the prior art application may further limit the maximum possible diameter of the connector screw(s) used, and may increase the likelihood of the fracture and failure of these implant components, above and beyond what has already been noted, when these components would be placed under normal significant functional load-of the posterior sections of the upper and lower jaws.

The following embodiments relate to the improved implant of Pat Application No. PCT/IB2010/050456, incorporated fully herein by reference, wherein the head component is of substantially similar dimensions as that described in WO Pat. App. No. 2006/082610; U.S. Pat. No. 2003/0180686.

In the case of a head component of substantially similar dimensions as the prior applications cited above, as only the connector screw needs to slide through the internal bore hole of the head component of the present invention and not the bone attachment component itself, the improved implant according to various aspects of the teachings herein makes possible the avoidance of the above mentioned design drawbacks of the prior art and allows for the use of bone attachment component(s) of greater structural diameter without the need of a headrest (larger diameter head section of the root screw mentioned above). Instead the distal portion of the bone attachment component may engage the exterior surface of the set rings on the bottom surface of the head component (e.g., the bone attachment component may be a root screw that is headless). Additionally, the diameter of the connector component according to some embodiments of the present improved implant can now be of greater diameter than the prior art applications described above. This novel design of the present invention translates into an implant that is structurally sound and has long-term viability and clinical success as compared to the high likelihood of catastrophic clinical failure and loss of the structurally unsound implants of the applications described above.

The novel head component according to some embodiments of the present invention describes design elements for the relating and securing of the bone attachment component(s) at a pre-determined angle to the head component (as was previously described) and which is at a different angle to the relation and securing of the separate abutment to the head component. The pre-determined angle of the relation and securing of the root screws to the head component can vary based, for example, on machining the angles of both the lower section of the internal bore hole shaft holes(s) and the bottom exterior surface indented set ring(s) while keeping the upper section of the internal bore shaft hole(s) mainly vertically straight. In the case of "multi-rooted" (e.g., having two or three bone attachment components) implants according to the teachings herein, these angled sections of the internal bore hole shafts can vary within the same head component. This means that each of these multiple bone attachment components can be related and tightly secured to the head component with connector components at pre-determined differing angles to each other at the time of the insertion of these endosseous (in bone) components in the fresh osteotomy (initial implantation) or alternatively, in the root sockets of a recently extracted tooth, due to the novel design according to the teachings herein which may also include angled limiting seat flanges incorporated in the lower section of the angled internal bore hole shafts of the head component to limit and fully seat circumferentially the screw head of the connector components (first connectors). The prior art applications described above do not allow for any of the above capabilities. In particular these applications do not incorporate in their head component design an internal limiting flange (rest seat) for the screw head of the connector component to seat down onto at all, and so do not allow for the head component and root screw to be tightly secured to each other at the time of initial implantation of these two endosseous (in bone) components into the freshly prepared bone preparation (osteotomy) or alternatively, in the root sockets of a recently extracted tooth. This is a major drawback of these applications for the reasons that were described earlier.

In both the delayed implanting surgical technique and even more so in the surgical technique known as immediate extraction-immediate implant surgical technique, the novel design of the present implant system offers the ability for the practitioner to review his diagnostic data on the patient (radiographs and CT scans of the jawbone) and choose prior to surgery the specific head component (which mimics the lost root trunk structure of the extracted tooth) that will allow for the securing to it of multiple bone attachment components, which mimic the structure of the extracted roots (wherein each bone attachment component may be of the same or different diameter and/or length), at same or different pre-determined angles that most closely match up to the natural angled root socket voids that will remain (in the recent extraction site) when the unsalvageable multi-rooted molar is extracted or (in the delayed implanting technique) which will fit into the target bone site most easily without damaging nearby sensitive anatomical structures such as the maxillary (upper jaw) sinus and the inferior alveolar nerve in the mandible. Therefore, reduced drilling, substantially no drilling, minimal drilling or even entirely no drilling would be required prior to the inserting of the improved multi-rooted implant of the present invention into the fresh extraction site sockets. Such reduction in necessary drilling preparation at the target bone site further translates into a potentially reduced or minimal amount of post-operative pain for the patient, potentially reduced healing time, as less bone needs to "fill-in" or adapt (osseointergrate or heal) around the improved implant of the present invention, or both. Reduced healing time means the implant can also be "functionally loaded" (chewed on with the crown glued onto its abutment) much sooner than was previously possible. None of the previously described prior art applications contains these features and capabilities.

The novel surgical guidance and delivery system of the present invention described above is accomplished with the following novel surgical method and novel surgical tools for accurately preparing the osteotomy (bone preparation) and inserting and assembling (securely connecting to each other) the implant components of the improved implants of the present invention.

Precision Implant Surgical Guidance System: In order to relate and control the dental handpiece (drill) to the osteotomy (which will be described below), a novel removable handpiece adaptor drill guide sleeve is attached to the "head" (working end) of the dental handpiece. The guide sleeve's ring or tube may have a slot cut in its side for the easier insertion and removal of the dental handpiece from it. The guide sleeve may have a hole or channel cut into its ring, which preferably is sufficient for the unimpeded flow of irrigating solution form the drill head. The irrigating solution may be employed for heat reduction, for removal of ground bone particles debris from the osteotomy, or both, while drilling into the target bone site. The guide sleeve preferably is such that it allows the following described steps to be performed.

The osteotomy (bone preparation using the delayed implanting procedure previously described) may be prepared in a plurality of distinct and different stages including a first stage and a second stage. The first stage may include one or any combination (e.g., all) of the following steps: preparing the top (distal) portion of the osteotomy at the target bone site which will allow for the accurate and/or precise insertion of the head component into it (which may be accomplished using the surgical jig described above with the head component drill guide attached to it); and inserting a milling-type dental drill bit into a dental handpiece to which the handpiece guide sleeve has been attached or alternatively the handpiece guide sleeve may be pre-attached onto the head component drill guide ring (first drill guide) and the hand piece drill then inserted into this assembly.

The practitioner may place the prepared handpiece drill over the assembled surgical jig (which preferably had been placed and positioned in relation to the crestal height and buccal and lingual plates, and secured over the target bone site). The practitioner may engage the handpiece guide sleeve onto the head component drill guide ring of said assembly. The practitioner may slide the handpiece guide sleeve in a downward direction while the drill is on. The handpiece guide sleeve may be slid vertically down a specified distance on a drill guide ring or tube until its limiting step feature encounters the limiting stop of the head component drill guide ring. This may create the initial controlled pilot depth cut into the target bone. The practitioner may then move the handpiece, which preferably is still connected via the sleeve guide to the head component drill guide ring, along the sliding tracks of the ring assembly either horizontally forward or backward.

As the head component drill guide slides generally horizontally along its tracks (which preferably is secured to the jig platform), a generally oval-shaped hole may be created as the milling drill bit engages the bone. (It will be appreciated that tracks that are not straight may result in a hole having a different shape, such as a kidney shape). The maximum length of the oval may be controlled based on the length of the tracks of the head component drill guide and the diameter of the milling drill bit. In this manner the depth, shape and dimensions of the upper (distal) portion of the osteotomy may be accurately controlled and accomplished by the surgical guidance system with a minimal amount of vibration to the surgical jig. This novel and improved method for preparing this segment of the osteotomy over the milling method used by PCT/IB 2010/050456 by the same inventor, is advantageous as it may significantly reduces the potential for dislodging the surgical jig from its previously secured position over the target bone implant site.

The practitioner may next insert the head component template (first template), placing it into the prepared oval hole (first stage of the osteotomy) in order to check the shape, depth of this first upper (distal) section of the bone preparation, the even flatness of the bony floor of this upper portion of the osteotomy, or any combination thereof. If required, one or more of the previous steps may be repeated or other remedial steps may be taken until the first stage of the osteotomy has a desired shape and/or size. The process may include a step of removing the first drill guide from the surgical jig, e.g., after the first section of the osteotomy has been completed and/or checked for accuracy of preparation.

The process may include a step of attaching the bore shaft drill guide assembly (second drill guide) at a specific location onto the surgical jig. The practitioner may at this stage place a standard drill bit for drilling bore shafts into a dental handpiece (with its guide sleeve ring or tube still attached to it), and may engage the bore shaft drill guide assembly. The process may include a step of sliding the handpiece guide sleeve in a downward direction while the drill is on. The handpiece guide sleeve preferably will slide generally vertically down in an angled or straight direction a specified distance until its limiting step feature encounters the limiting stop of the bore shaft drill guide ring. The bore shaft ring or tube may be produced at different angles allowing for the preparation of variously angled bore shafts. In such manner the lower (proximal) portion (second stage) of the osteotomy may be prepared yielding an accurately angled or straight bore shaft of specific diameter and depth. The diameter and depth of the bore shafts may be altered by inserting into the dental drill different diameters or lengths of the drill bit (e.g., until a desired diameter and/or depth is achieved).

If the lower (proximal) portion (second stage) of the osteotomy requires a second bore shaft preparation (to accommodate a second bone attachment component of the improved multi-root implant of the present invention) then the bore shaft drill guide assembly may be removed from the surgical jig, rotated 180 degrees and secured back onto the surgical jig. A second bore shaft may be prepared in like manner to the first bore shaft and at a pre-determined distance and angle relative to the first bore shaft that preferably is controlled by the new position of the bore shaft drill guide assembly and the drill bit chosen by the practitioner.

To prepare the second bore shaft at an entirely different degree of angulation than the first bore shaft, a different bore shaft drill guide assembly whose drill guide tube is made at a different angle than the first bore shaft drill guide may at this stage be used for this surgical step. As such, the process may include a step of replacing the bore shaft drill guide assembly. If a third bore shaft at yet a different angle and location is required, then a different third bore shaft drill guide may be attached, and a third bore shaft may be drilled.

The process may include one or more steps of checking a bore shaft with the bore shaft template, e.g., by placing the template into the lower (proximal) portion of the osteotomy. This step may include checking the depth of one or more bore shafts. The bore shaft template may have notches or other markings (e.g., on its side) that correspond to depths (e.g., in units of millimeters).

Once the lower (proximal) portion of the multi-stage osteotomy has been checked, the first stage and second stage of the bone preparation of the present invention is now accomplished. It will be appreciated that one or more additional stages may be used in the osteotomy. However, an osteotomy having exactly two stages is preferred. When the osteotomy is completed, it is now ready for the accurate insertion and relating to each other of the endosseous implant components, such as an improved implant according to the teachings herein.

Precision Implant Component Delivery System: The precision implant component delivery system is such that it allows for one or more (e.g., all) of the following described process steps to be employed. The process may include a step of bringing the root screw driver that has been attached to a bone attachment component via its engaging elements to the corresponding engaging elements on the head of the bone attachment component. The root screw driver may further be secured to the bone attachment component via screwing its novel separate inner screw into the inner threaded bore hole sleeve of the bone attachment component. The bone attachment component may be inserted into the lower portion (bore shaft) of the already prepared two stage osteotomy. The engaged novel inner screw of the root screw driver provides for greater torque force when screwing in the bone attachment component into the bone bore shaft, or alternatively, in the root sockets of a recently extracted tooth, as well as preventing the undesirable "unscrewing" of the root screw from the prepared bone bore shaft when the root screw driver is disengaged from the root screw (by unthreading the inner screw from the threaded bore hole of the root screw) after the root screw has been screwed into the bone bore shaft preparation.

The process of installing the implant may include a step of inserting the attached root screw driver component into the bore shaft drill guide assembly that is attached to the surgical jig and screwing down the bone attachment component into the prepared bone bore shaft until the driver's limiting step engages the limiting step of the bore shaft drill guide tube. In such manner the bone attachment component may be placed accurately at the proper angle, location and depth into the lower (proximal) portion (second stage) of the osteotomy. This accurate placement of the bone attachment component(s) may be critical to allow for the later precise and intimate relation of said distal end(s) of the bone attachment component(s) to the mesial surfaces (bottom) of the head component.

The process of installing the implant may include a step of inserting p the root screw template into the upper portion of the osteotomy to check the exact height, angle, and location that the top (distal end) surface of the bone attachment component "sticks up" into the void of the upper section of the osteotomy above the bony floor of said section of the bone preparation (this height should ideally correspond to the angle, depth, and location of the indented set rings on the exterior undersurface of the head component once said component is to be placed onto the bone attachment component(s)). If these parts are not accurately related to each other, a microgap may be created between these two implant components. Such a microgap could possibly allow for micro-infiltration of pathogenic bacteria and bone loss around these implant parts, an undesirable result as has previously been described.

If necessary, the bone attachment component's height may be adjusted using the root screw driver and checked again with the second template. Once it has been determined that all the bone attachment component(s) are screwed into the bore shaft(s) at the exact proper height and their respective heights are even with each other, the head component indented undersurface set ring(s) may be positioned over bone attachment component(s) and the head component may be inserted into the upper (distal) section of the osteotomy, or alternatively, the root trunk void of the recently extracted tooth, and secured in a very intimate and tight manner to the bone attachment component(s) with the connector components(s), to secure the implant components of the present invention into the jawbone (endosseous implant components).

Alternatively, to save time, after drilling each bore shaft, a bone attachment component may be screwed into the freshly prepared bore shaft, checked for its position with the templates provided, and then the first bore shaft drill guide is replaced by a new bore shaft drill guide to prepare the next bore shaft into which the next bone attachment component may be screwed in with the root screw driver and both bone attachment components may then be checked to each other (e.g., prior to placing the head component over them and screwing the head component tightly down onto them, so that the head component is drawn in a compressive state).

The process may include a step of placing a temporary cover screw(s) in the upper (distal) portion of each bore hole(s) of the head component. Preferably, the temporary cover screw sufficiently covers the bore hole so that in-growth of bone in the bore hole is reduced or more preferably prevented (e.g., while the bone adapts to the inserted implant (osseo-integration)).

At the same visit or at a subsequent visit (to allow for osseointegration) an abutment may be secured to the head component using the abutment screw(s). A crown may be fabricated and attached using common techniques known in the dental field.

In various aspects of the present invention, a temporary (surgical stage) connector screw may be fitted between the head component and the bone attachment component which is replaced after healing (osseo-integration of the head component and/or bone attachment component) with a final (prosthetic stage) connector screw. The final connector screw may be used to connect and tightly secure an abutment to the head component and the bone attachment component.

The drawings herein, though not necessarily drawn to scale, are part of the teachings herein and depict examples within the scope of the general teachings. Even if not explicitly recited verbally, the drawings are contemplated as part of the teachings herein for, among other things, the relative positions of the various features shown, the general geometries shown, the relatively proportions shown, the general orientations shown and the like. Even if not specifically stated, variations to the embodiments of the examples in the drawings are contemplated as within the scope of the teachings. For example, unless otherwise apparent from the teachings, relative proportions may vary (e.g., by 20%, 40%, 60% or more than as shown), curved surfaces depicted may include one or more flat surfaces, flat surfaces may include one or more curved surface, or any combination thereof.

Reference is now made to FIG. 1a is a cross-section profile sketch of a root screw design 42 of the prior art wherein is depicted its larger diameter head with limiting bottom surface step 42a, it body 42b and the diameter of its body, 42c.

FIG. 1b is a cross-section profile sketches of another root screw design 43 of the prior art wherein is depicted its larger diameter head with limiting step 43a, an internal sleeve 43c with side walls 43d, and a body 43b. Also depicted is the diameter of the body 43e which has the same dimension as the diameter 42c of the prior art root screw 42 depicted in FIG. 1a FIG. 1c is a cross-section profile sketch of FIG. 1b (prior art) which has been modified by thickening the body of the prior art root screw 43 of FIG. 1a by adding the areas 44 to both side walls along the entire body 43b of the prior art root screw 43.

FIG. 1d is a cross-section profile sketch of FIG. 1c (prior art) which has been further modified by cross-hatching the limiting step head 43a as areas 45, further delineating the two areas 46 on both sides of the inner walls of the internal sleeve 43c.

FIG. 1e is a cross-section profile sketch of the root screw of the present invention still showing modified areas that remained after adding areas 44 and removing areas 45 and 46.

FIG. 1f is a cross-section profile sketch of the root screw 48 of the present invention wherein is depicted the side walls 48a (which are thicker than the side walls 43d of the prior art) the internal sleeve 47 (which is wider than the internal sleeve 43c of the prior art 43) and the diameter of the body 48b (which is wider than the body 43e of the prior art 43).

FIG. 1g is a cross-section profile side by side comparison of the prior art root screw 43 and the root screw 48 of the root screw of PCT/IB 2010/050456.

FIG. 2a is a cross-section profile sketch illustrating the prior art root screw 42 of a narrow diameter 50 of the connector hole 49b with its head 42a resting internally on the limiting circumferential flange 49a of the connector hole 49b of the head component profile 49 and showing the relation of the prior art root screw component 42 to the prior art head component 49. Also depicted is the internal diameter 50a and external diameter 50b of the prior art head component 49.

FIG. 2b is a cross-section profile sketch illustrating another prior art root screw 43 of a narrow diameter 50 of the connector hole 49b with its head 43a resting internally on the limiting circumferential flange 49a of the connector hole 49b of the head component profile 49 and showing the relation of the prior art root screw component 43 to the prior art head component 49. Also depicted is the same internal diameter 50a and external diameter 50b dimensions of the prior art head component 49 of FIG. 2a.

FIG. 2c is a cross-section profile sketches illustrating the relation of the head component profile 39 to the root screw component profile 36 of the improved implant of the present invention wherein is depicted the large diameter 40 of the roots screw profile 36 and the greater thickness of the side walls 36a (as compared to the side walls 31d of the prior art). Also depicted is the areas 39b which will be removed to expand the diameter of the connector hole 37a as well as the same internal diameter 40a and external diameter 40b dimensions of the head component profile 39 of the referenced prior art patent PCT/IB 2010/050456 as was seen in the prior art head component 37 of FIGS. 2a and 2b.

FIG. 2d is a cross-section profile sketches illustrating the relation of the head component profile 51 to the root screw component 48 of the referenced prior patent PCT/IB 2010/050456 wherein the internal sleeve 47 is of greater diameter than the internal sleeve 43c of the prior art root screw 43 of FIG. 2b. Also depicted is the new limiting circumferential flange profile 51c and the larger connector hole diameter 51d (compared to the connector hole 49b of the prior art root screws 42 and 43 of FIGS. 2a and 2b.

Figure 3A:
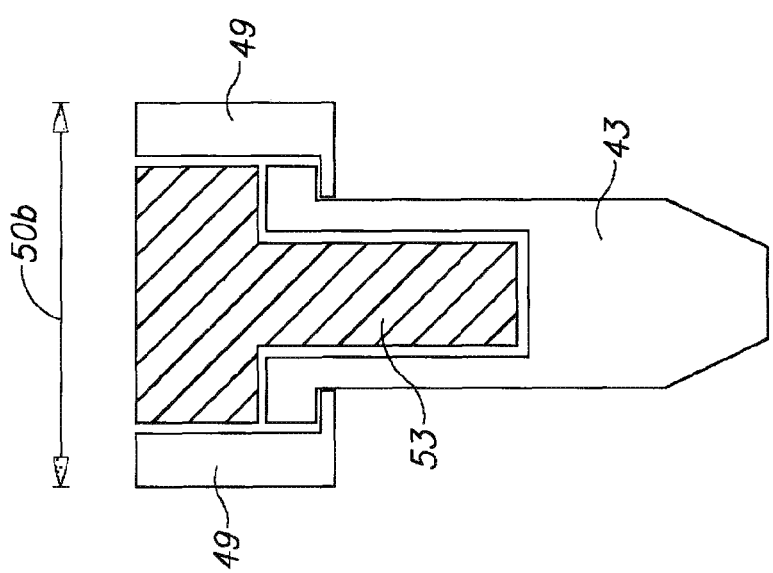
FIG. 3a is an illustrative cross-section profile sketch illustrating the prior art relation between the head component profile 49, the root screw component profile 43 and the connector screw profile 53 that secures these two components to each other.

FIG. 3a is a cross-section profile sketch illustrating the prior art relation between the head component 49, the prior art root screw component 43 and the prior art connector screw 53 that secures these two components to each other. Also depicted is the external diameter dimension 50b of the head component 49.

FIG. 3b is a cross-section profile sketch illustrating the relation between the head component 51, the root screw component 48 and the connector screw 54 that secures these two components to each other of the referenced prior patent PCT/IB 2010/050456. Also depicted is the same external dimension 50b (seen in FIG. 3a) of the head component 51.

FIG. 4a is a length-wise cross-sectional view of the prior art dental implant wherein are depicted the root screw 1, the head component 2, the abutment 3 and the connector screw 4.

FIG. 4b is a length-wise cross-sectional view of one embodiment of the dental implant of the prior art PCT/IB2010/050456 of which the present invention is in part a derivative thereof wherein is depicted the root screw 1, the head component 2, the upper segment of the internal bore hole shaft 2a, the lower segment of the internal bore hole shaft 2b, the limiting seat circumferential flange 2r of the lower segment 2b, the connector screw 4, the abutment 3 and the abutment screw 5. FIG. 4c is a length-wise cross-sectional view of one embodiment of the present invention wherein are depicted the head component 2, the limiting seat circumferential flange 2r of the internal bore hole shaft 2m, the root screw 1, and the temporary connector screw (surgical stage) 4a.

FIG. 4d is a length-wise cross-sectional view of one embodiment of the present invention wherein are depicted the head/component 2, the limiting seat circumferential flange 2r of the internal bore hole shaft 2m of the root screw 1, the abutment 3, and the final connector screw (prosthetic stage) 4b.

FIG. 5a is a length-wise cross-sectional view along the bucco-lingual (cheek to tongue) axis of one embodiment of the endosseous (in bone) components 6a of one embodiment of the dental implant 6 of the present invention wherein are depicted the head component 2, the limiting seat circumferential flange 2r, the smaller diameter distal neck 1a and threaded internal bore hole sleeve 1b of the root screw 1, and the temporary connector screw (surgical stage) 4a.

FIG. 5b is a length-wise view along the mesio-distal (front to back) axis of one embodiment of the endosseous components 6a comprised of the root screw 1 and the connector screw 2 of the dental implant 6 of the present invention.

FIG. 5c is a length-wise view along the bucco-lingual (cheek to tongue) axis of one embodiment of the dental implant 6 of the present invention.

FIG. 5d is a length-wise cross-sectional view along the mesio-distal (front to back) axis of one embodiment of the endosseous components 6a of the dental implant 6 of the present invention wherein are depicted the cut out slots 2s on the top (distal) surface 2i of the head component 2.

FIG. 5e is a length-wise cross-sectional view along the bucco-lingual (cheek to tongue) axis of one embodiment of the entire dental implant 6 including the abutment 3 of the present invention wherein is depicted the final (prosthetic stage) connector screw 4b.

FIG. 5f is a length-wise view along the mesio-distal (front to back) axis of one embodiment of the entire dental implant 6 of the present invention wherein are depicted the endosseous (in bone) components 6a and the above the bone level abutment 3.

FIG. 5g is a length-wise view along the bucco-lingual (cheek to tongue) axis of one embodiment of the entire dental implant 6 including the abutment 3 of the present invention.

FIG. 5h is a length-wise cross-sectional view along the mesio-distal (front to back) axis of one embodiment of the entire dental implant 6 of the present invention wherein are depicted the limiting seat circumferential flange 3a of the abutment 3 and the threaded internal bore hole sleeve 1b of the root screw 1.

FIG. 5i is a top view of one embodiment of the head component 2 of the present invention wherein are depicted a raised border 2t on the top surface 2i, a countersunk center area 2v, and an internal horizontal multi-lobed petal locking element of the head component 2.

FIG. 6a is a cross-sectional view along the mesio-distal axis of PCT/IB 2010/050456 wherein are depicted the upper section 2a with its threaded internal walls 2e of the internal bore hole shaft 2m, the lower section 2b with its limiting seat circumferential flange of the internal bore hole shaft 2m, the proximal (bottom) surface 2k, the distal (top) surface 2i, the external side walls 2j, with microgrooves 2g and its beveled superior edge 2f, the inset set ring sockets 2d in its proximal surface 2k and the narrower diameter segment 2c of the lower section 2b of the head component 2.

FIG. 6b is cross-sectional view along the mesio-distal axis of one embodiment of the head component 2 of the present invention wherein are depicted the internal bore hole shaft 2m with its upper section 2a with its threaded internal walls 2e, the lower section 2b which is angled in relation to the upper section 2a, the area that is left unthreaded 2p and angled area 2h of the upper section 2a which aligns for manufacturing purposes with the same angle as the lower section 2b, the inset set ring sockets 2d angled to match the angle of the lower section 2b above it, with its angled rest seat 2o, the limiting rest seat 2r of the lower section 2b to limit the head of the connector screw 4, the larger diameter 2l of the upper segment of the lower section 2b and the smaller diameter 2c of the lower segment of the lower section 2b.

FIG. 6c is cross-sectional view along the mesio-distal axis of yet a further embodiment of the head component 2 of the present invention wherein are depicted similar features as those depicted in FIG. 6b with a change in the shape of the inset set ring sockets 2d to a spherically concave shape of the circumferential limiting seat 2w.

Figure 7G:
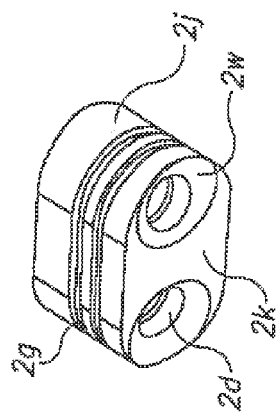
FIG. 7g is an illustrative angled side/bottom view of the head component of FIG. 6b.
Figure 7H:
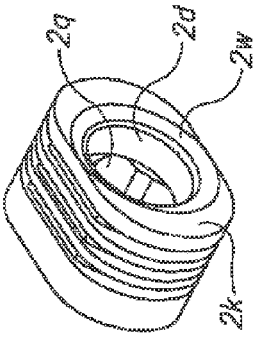
FIG. 7h is an illustrative angled side/bottom view of the head component of FIGS. 5a-5h.
Figure 7I:
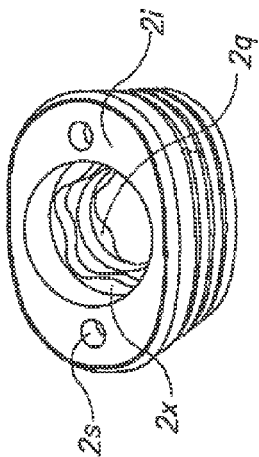
FIG. 7i is an illustrative angled top/side view of the head component of FIGS. 5a-5h.
Figure 7D:
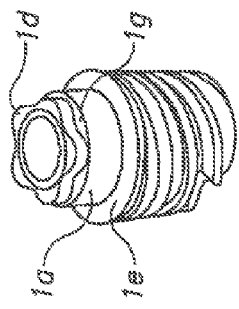
FIG. 7d is an illustrative angled front view of another root screw 1 showing features of a root screw according to the teachings herein.
Figure 7E:
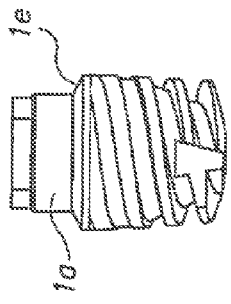
FIG. 7e is a side view of the root screw 1 of FIG. 7d.
Figure 7F:
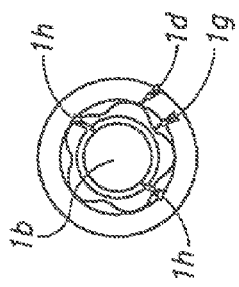
FIG. 7f is an illustrative top view of the root screw 1 of FIG. 7d.
Figure 7A:
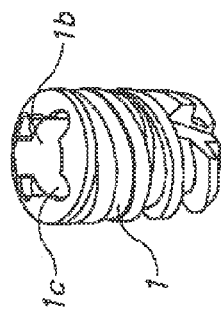
FIG. 7a is an illustrative angled front view of a root screw 1 according to the teaching herein.

FIG. 7a is an angled front view of one embodiment of the root screw 1 of the present invention wherein are depicted cut out slots 1c in the inner lip of the spherically convex shape 1f, and the internal bore hole sleeve 1b.

Figure 7B:
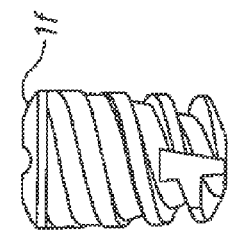

FIG. 7b is a side view of the embodiment of the root screw 1 of FIG. 7a wherein is depicted the profile of the convex spherical shape 1f of the distal end of the root screw 1.

Figure 7C:
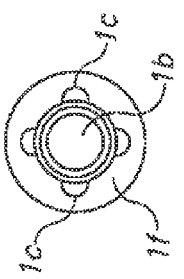

FIG. 7c is a top view of the embodiment of the root screw 1 of FIG. 7a wherein are depicted the cut out slots 1c, the spherically convex distal end 1f, and the internal threaded bore hole sleeve 1b.

FIG. 7d is an angled front view of another embodiment of the root screw 1 of the present invention wherein are depicted the smaller diameter neck 1a, the petal-shaped connecting element 1d, the circumferential limiting seat 1g of the top of the neck 1a and the spherically convex collar 1e.

FIG. 7e is a side view of the embodiment of the root screw 1 of FIG. 7d wherein are depicted the neck 1a, the spherically convex collar 1e.

FIG. 7f is a top view of the embodiment of the root screw 1 of FIG. 7d wherein are depicted the internal threaded bore hole sleeve 1b, the beveled lip 1h of the inner lip of the threaded bore hole sleeve 1b, the petal shaped connector element 1d, and the circumferential limiting seat 1g of the top of the neck 1a.

FIG. 7g is an angled side/bottom view of the head component of FIG. 6b wherein are depicted the inset set ring bore hole collar 2d with its spherically concave circumferential limiting seat contour 2w in the proximal (bottom) surface 2k, and the microgrooves 2g cut into the side walls 2j.

FIG. 7h is an angled side/bottom view of the head component of FIGS. 5a-5h wherein are depicted the petal shaped connector element 2q which lies in the lower section 2b of the internal bore hole shaft 2m, and the inset set ring bore hole collar 2d with its spherically concave circumferential limiting seat contour 2w on the bottom surface 2k.

FIG. 7i is an angled top/side view of the head component of FIGS. 5a-5h wherein are depicted the cut outs 2s on distal surface 2i, the petal shaped connector element 2x which lies in the bottom of the upper section 2a of the internal bore hole shaft 2m, and the petal shaped connector element 2q which lies at the bottom of the lower section 2b of the internal bore hole shaft 2m. Of course, other shaped connector elements may be used.

FIG. 8a is side view along the mesio-distal axis of one embodiment of the entire dental implant 6 of the present invention wherein are depicted the angled root screws 1, the oval head component 2 with its cut out slots 2s to receive the positioning/retentive pins 3h of the oval abutment 3.

FIG. 8b is a see-through side view along the mesio-distal axis of one embodiment of the entire dental implant 6 of the present invention wherein are depicted the angled root screws 1, the connector screws 4, the oval head component 2, the oval abutment 3, and the head 5a and threaded body 5b of the abutment screws 5.

FIG. 8c is a semi-transparent side view along the mesio-distal axis of another embodiment of the entire dental implant 6 of the present invention wherein are depicted the angled root screws with spherically convex distal end 1f, the spherically concave circumferential limiting seat 2w of the inset set ring 2d of the head component 2 into which the matching convex distal end 1f of the root screw seats, the concave bottom 5c to the threaded body 5b of the abutment screw 5 and the concave projecting gingival collar 3b of the abutment 3.

FIG. 9a illustrates three different views of one embodiment of the head component drill guide assembly 8 wherein are depicted the drill guide ring 8a, the cut out sliding tracks 8d of the base 8b, and the side cut out 8c of the drill guide ring 8a and the drill guide hole 8e.

FIG. 9b illustrates four different views of one embodiment of the bore shaft drill guide assembly 9 wherein are depicted the angled drill guide ring 9a, the side cut out slots 9c of the angled drill guide ring 9a, the attachment cut outs 9d in the base 9b, the angled surface 9f of the base beneath the drill guide ring 9a and the drill guide hole 9e.

FIG. 10a is a side view along the mesio-distal axis wherein is depicted one embodiment of the surgical jig 7 to which has been attached the head component drill guide assembly 8 and a dental handpiece 16 with a milling drill bit 17 inserted in it above the handpiece drill guide sleeve 14. Also illustrated are the adjacent teeth, the premolars 25, and the molar 26.

FIG. 10b is a side view along the mesio-distal axis wherein is depicted one embodiment of the surgical jig 7 to which has been attached the head component drill guide assembly 8 and a dental handpiece 16 fully inserted into the handpiece drill guide sleeve 14.

FIG. 10c is a side view along the mesio-distal axis wherein is depicted one embodiment of the surgical jig 7 to which has been attached the bore shaft drill guide assembly 9 and a dental handpiece 16 above it with a twist drill bit 18 inserted in it.

FIG. 10d is a side view along the mesio-distal axis wherein is depicted one embodiment of the surgical jig 7 to which has been attached the bore shaft drill guide assembly 9 and one embodiment of the root screw driver 37 with an attached root screw 1 above the bore shaft drill guide 9.

FIG. 10e is a side view along the mesio-distal axis wherein is depicted one embodiment of the surgical jig 7 to which has been attached the bore shaft drill guide assembly 9 and one embodiment of the root screw driver 37 with an attached root screw 1 fully inserted into the bore shaft drill guide assembly 9 until the limiting stop 38a of the body 38 of the root screw driver 37 is resting on the top of the ring 9a of the bore shaft drill guide.

FIG. 10f is a side/bottom view along the mesio-distal axis of one embodiment of the abutment 3 of the present invention wherein are depicted an extending neck 3c form its proximal (bottom) surface 3j, an inner bore shaft 3f, a limiting circumferential seat 3g, a petal-shaped connector element 3d which will engage a matching petal-shaped connector element 2x of one embodiment of the head component 2 which is illustrated in FIG. 7i.

FIG. 10g is a side/bottom view along the mesio-distal axis of another embodiment of the abutment 3 of the present invention wherein are depicted a gingival collar 3b, positioning/retentive pins 3h, and the inner bore shafts 3f.

FIG. 10h is a top view along the mesio-distal axis of another embodiment of the abutment 3 of FIG. 10g wherein are depicted the limiting circumferential seat 3a onto which seats the head 5a of the abutment screw 5, the inner bore shafts 3f, the distal (top) surface 3i, and the cut out 3k between the inner bore shafts 3f.

Figure 11A:
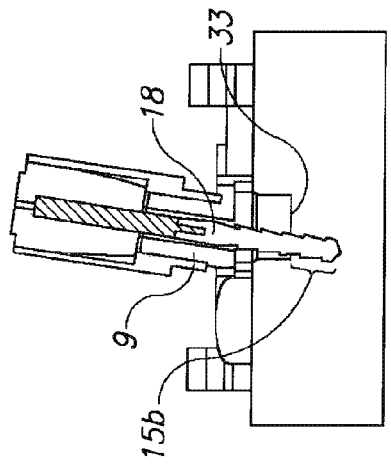
FIG. 11*a* is an illustrative cross-sectional length-wise view of a dental handpiece head 16 with a milling drill bit 17 inside it and with a handpiece drill guide sleeve 14 attached to a surgical jig 7 according to the teachings herein.

FIG. 11a is a cross-sectional length-wise view of the dental handpiece head 16 with a milling drill bit 17 inside it and with the handpiece drill guide sleeve 14 attached to it, fully engaged on an embodiment of the head component drill guide ring 8a of the head component drill guide assembly 8 and illustrating the initial pilot depth drilling hole 40 for the upper segment 15a of one embodiment of the two stage osteotomy 15.

Figure 11B:
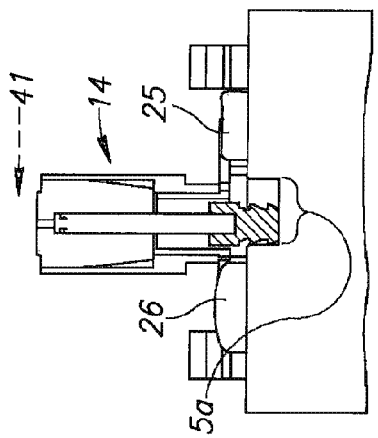
FIG. 11*b* is an illustrative cross-sectional length-wise view illustrating a sliding 41 of a head component drill guide assembly 8 which may allow a milling drill bit 17 to mill a pre-determined dimension and depth upper segment 15*a*, such as for a first stage of a two stage osteotomy 15. The first stage 15*a* may have a generally oval cross-sectional shape.

FIG. 11b is a cross-sectional length-wise view illustrating the sliding 41 of the head component drill guide assembly 8 which allows the milling drill bit 17 to mill a specific dimension and depth oval upper (first stage) segment 15a of the two stage osteotomy 15.

Figure 11C:
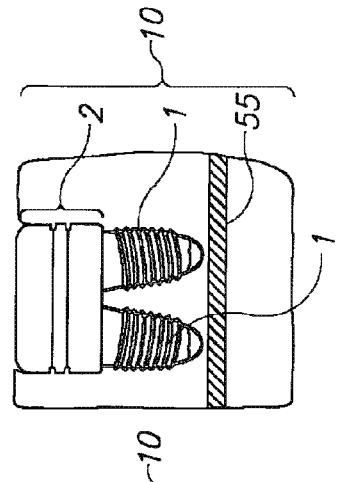
FIG. 11*c* is an illustrative cross-sectional length-wise view illustrating a dental handpiece head 16 with a bore shaft twist drill bit 18 inside it and with a handpiece drill guide sleeve 14 attached to it, fully engaged on over an angled bore shaft drill guide assembly 9 preparing a lower (proximal) segment (e.g., second stage) into the bony floor 33 of the upper segment 15*a*, such as for a two stage osteotomy 15. The second stage may include, or consist essentially of a first bore shaft 15*b*.

FIG. 11c is a cross-sectional length-wise view illustrating the handpiece head 16 with a bore shaft twist drill bit 18 inside it and with the handpiece drill guide sleeve 14 attached to it, fully engaged on over an embodiment of an angled bore shaft drill guide assembly 9 preparing the first bore shaft 15b into the bony floor 33 of the upper segment 15a of the two stage osteotomy 15 (which now becomes the lower second stage segment 15b of the two stage osteotomy 15).

Figure 11D:
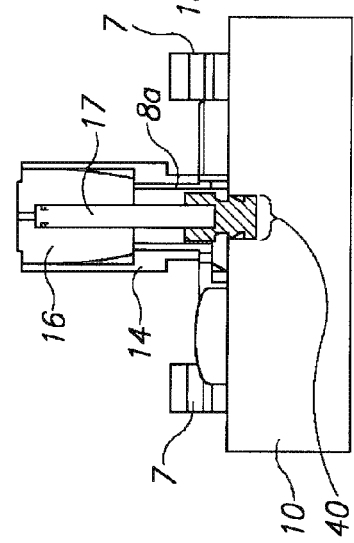
FIG. 11*d* is an illustrative cross-sectional length-wise view illustrating a dental handpiece head 16 with a bore shaft twist drill bit 18 inside it and with a handpiece drill guide sleeve 14 attached to it, fully engaged on over an angled bore shaft drill guide assembly 9 preparing a second bore shaft 15*b* into a different location of the floor of an upper segment 15*a* (of a two stage osteotomy 15) at a different angle to a first bore shaft 15*b* of the lower segment of the two stage osteotomy 15. The second stage may include or consist essentially of two bore shafts 15*b*.

FIG. 11d is a cross-sectional length-wise view illustrating the handpiece head 16 with a bore shaft twist drill bit 18 inside it and with the handpiece drill guide sleeve 14 attached to it, fully engaged on over an embodiment of an angled bore shaft drill guide assembly 9 preparing a second bore shaft 15b into a different location (in relation to the first bore shaft 15b) of the bony floor 33 of the upper segment 15a (of the two stage osteotomy 15) at a different angle to the first bore shaft 15b of the lower segment of the two stage osteotomy 15.

Figure 11E:
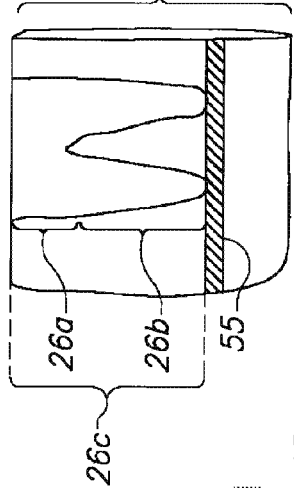
FIG. 11*e* is an illustrative cross-sectional length-wise view illustrating features of a natural lower molar extraction socket 26*c*.

FIG. 11e is a cross-sectional length-wise view illustrating the natural lower molar extraction socket 26c wherein are depicted the root trunk socket void 26a and the root sockets 26b in a section of the mandible 10 and the inferior alveolar nerve 55.

Figure 11F:
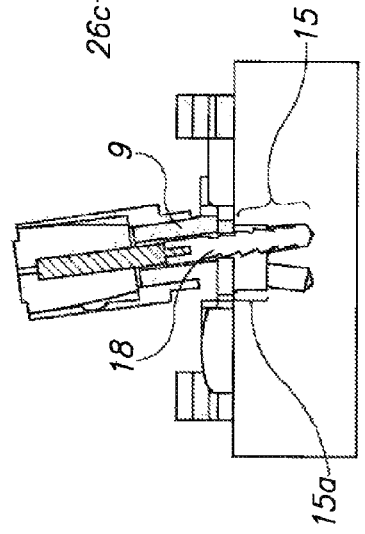
FIG. 11*f* is an illustrative cross-sectional lengthwise view illustrating a head component 2 and two angled root screws 1 secured to the head component.

FIG. 11f is a cross-sectional lengthwise view illustrating the head component 2 and two angled root screws 1 secured to each other within the extraction socket 26c of FIG. 11e wherein are depicted the inferior alveolar nerve 55 in the section of the mandible 10.

Figure 12A:
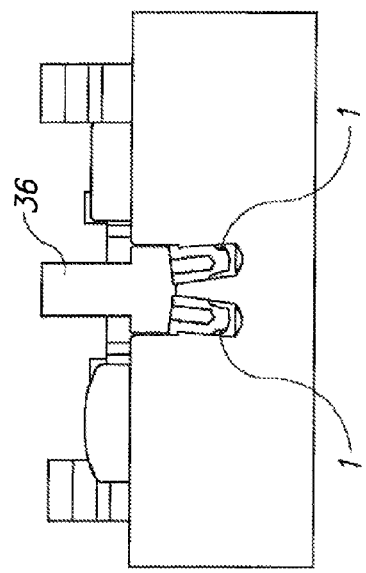
FIG. 12*a* is an illustrative cross-sectional length-wise view showing features according to the teachings herein of a root screw driver 37 engaging a root screw 1 while being fully inserted into a bore shaft drill guide assembly 9 and screwing the root screw component 1 to its proper location, angle and depth in a previously prepared bore shaft 15*b*, such as the bore shaft of FIG. 11*c*.

FIG. 12a is a cross-sectional length-wise view illustrating one embodiment of the root screw driver 37 engaging one root screw 1 with its inner screw 39 while being fully inserted into the bore shaft drill guide assembly 9 and screwing the root screw component 1 to its proper location, angle and depth in the previously prepared bore shaft 15b of FIG. 11c.

Figure 12B:
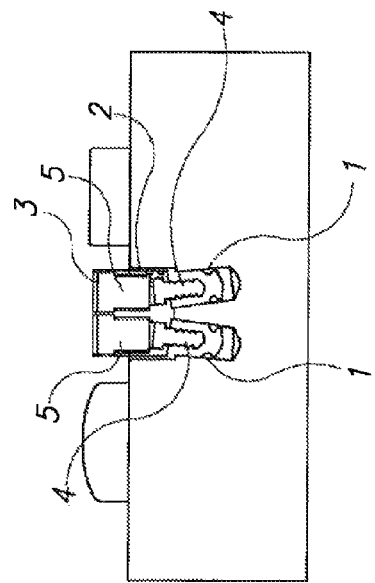
FIG. 12*b* is an illustrative cross-sectional length-wise view showing features according to the teachings herein of a head component-root screw depth template 36 fully inserted into an upper segment 15*a* (e.g., first stage) and seated onto the top surface 1*a* of one or more root screws 1.

FIG. 12b is a cross-sectional length-wise view illustrating one embodiment of the head component-root screw depth template 36 fully inserted into the upper segment 15a (first stage) and seated down onto the top (distal) surfaces of the root screws 1.

Figure 12C:
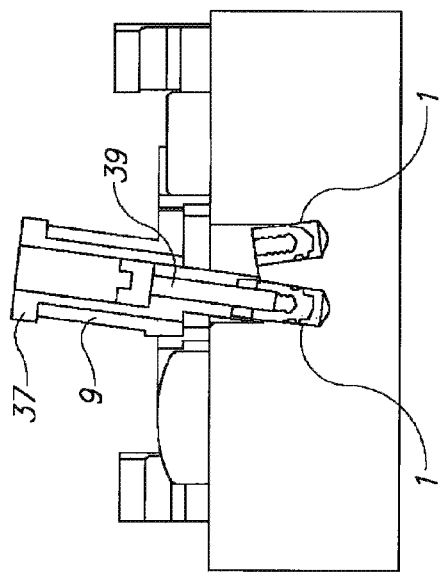
FIG. 12*c* is an illustrative cross-sectional length-wise view illustrating multi-root endosseous components of an implant 6 according to the teachings herein, wherein a head component 2 has been inserted (e.g., fully inserted) into an upper segment 15*a* (e.g., first stage) of the two stage osteotomy 15 and placed intimately over the top surfaces of two angled root screw components 1 and secured to them via two connector screws 4. The two connector screws may be angled to the same orientation as the root screws 1.

FIG. 12c is a cross-sectional length-wise view illustrating one embodiment of the multi-root endosseous components of the implant 6 of the present invention wherein the head component 2 has been fully inserted into the upper segment 15a (first stage) of the two stage osteotomy 15 and placed intimately over the top surfaces 1a of the two angled root screw components 1 and secured to them via two connector screws 4 angled to the same orientation as the root screws 1.

Figure 12D:
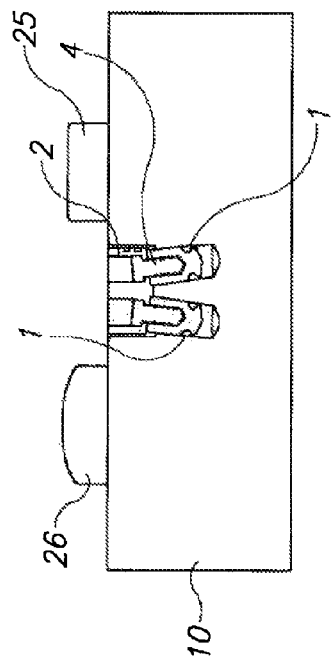
FIG. 12*d* is an illustrative cross-sectional length-wise view an entire multi-root implant 6 according to the teachings herein, wherein an abutment component 3 has been positioned over a head component 2 and secured to it via two abutment screws 5.

FIG. 12d is a cross-sectional length-wise view illustrating one embodiment of the entire multi-root implant 6 of the present invention wherein the abutment component 3 has been positioned over the head component 2 and tightly secured to it via two abutment screws 5.

FIG. 13a is a top view along the mesio-distal axis of the surgical jig 7 placed on a segment of the mandible 10 wherein are depicted the target bone site 11 as seen through the platform cut out 7b of the surgical jig 7.

FIG. 13b is a top view along the mesio-distal axis of the surgical jig 7 placed on a segment of the mandible 10 wherein is depicted one embodiment of the prepared distal upper portion 15a of the two stage osteotomy 15 of the present invention.

FIG. 13c is a top view along the mesio-distal axis of the surgical jig 7 placed on a segment of the mandible 10 wherein is depicted one embodiment of one bore shaft 15b prepared into the bony floor 33 of the upper portion 15a of the two stage osteotomy 15 of the present invention.

FIG. 13d is a top view along the mesio-distal axis of the surgical jig 7 placed on a segment of the mandible 10 wherein is depicted one embodiment of two bore shafts 15b prepared into the bony floor 33 of the upper portion 15a of the two stage osteotomy 15 of the present invention.

FIG. 13e is a top view along the mesio-distal axis of the surgical jig 7 placed on a segment of the mandible 10 wherein is depicted one embodiment of top segments 1f of the two root screws 1 screwed into the two bore shafts 15b prepared into the bony floor 33 of the upper portion 15a of the two stage osteotomy 15 of FIG. 13d.

FIG. 13f is a top view along the mesio-distal axis of the surgical jig 7 placed on a segment of the mandible 10 wherein is depicted one embodiment of the head connector 2 inserted into the upper portion 15a of the two stage osteotomy 15 and sitting directly on top of the two root screws 1 previously screwed into the bores shafts 15b of FIG. 13e.

FIG. 14a illustrates a lengthwise cross-sectional view of one embodiment of the body 38 root screw driver 37 wherein are depicted the limiting circumferential seat 38a, the inner shaft 38b, the side walls 38c, the engaging elements 38e, the inner threaded area 38g and the circumferential notch 38f for a rubber o ring, not illustrated.

FIG. 14b illustrates a lengthwise cross-sectional view of the body 38 of the root screw driver 37 and one embodiment of the internal adjustable screw 39 partially inserted into it.

FIG. 14c illustrates a lengthwise cross-sectional view of the body 38 of the root screw driver 37 and one embodiment of the inner adjustable screw 39 fully inserted into it.

FIG. 14d illustrates the lengthwise view of another embodiment of the body 38 with its limiting circumferential seat 38a and engaging end 38e of the root screw driver 37.

FIG. 14e illustrates the lengthwise view of one embodiment of the inner adjustable screw 39 of the root screw driver 37 wherein are depicted the adjusting knob 39c, the upper threaded area 39a which engages the inner threaded area 38g of the body 38, and the threaded end segment 39b which engages the internal threaded sleeve of the root screw 1.

FIG. 14f illustrates the lengthwise view of one embodiment of the inner adjustable screw 39 fully inserted into the body 38 of the root screw driver 37.

FIG. 14g illustrates the lengthwise view of one embodiment of the inner adjustable screw 39 fully inserted into the body 38 of the root screw driver 37 and to which has been attached one embodiment of the root screw 1.

FIG. 14h illustrates the lengthwise view of another embodiment of the body 38 of the root screw driver 37.

FIG. 14i illustrates the lengthwise view of another embodiment of the inner adjustable screw 39 of the root screw driver 37.

FIG. 14j illustrates the lengthwise view of the inner adjustable screw 39 of FIG. 14i fully inserted into the body 38 of the root screw driver 37.

FIG. 14k illustrates the lengthwise view of the inner adjustable screw 39 of FIG. 14i fully inserted into the body 38 of the root screw driver 37 and to which has been attached one embodiment of the root screw 1.

FIG. 14l is a close-up angled "see-through" view of one embodiment of the two stage osteotomy 15 wherein the threaded body of one root screw component 1 has been screwed down into one of the angled bore shafts 15b and the top angled portion of the root screw 1f is sitting in the empty void (above the bony floor 33) of the upper segment 15a of the two stage osteotomy 15.

FIG. 14m is a close-up top view of the two stage osteotomy 15 with two embodiments of the root screws 1 fully screwed into the bore shafts 15b and the distal (top) portions 1f of the root screws 1 sitting above the bony floor 33 of the upper portion 15a of the of the two stage osteotomy 15. Also depicted are the side walls 32 of the upper portion 15a of the two stage osteotomy 15.

FIG. 15a is a top/side angled view along the mesio-distal axis of one embodiment of the surgical jig 7 wherein are depicted the platform cut out 7b, the clamping arms 7c, the platform top surface 7a, the retentive cut out holes 21 for the placement of dental composite material, the swiveling locking knobs 20 with their threaded separating platforms 24 and the adjustable bony plate positioning elements 19.

FIG. 15b is a top/side angled view along the mesio-distal axis of another embodiment of the surgical jig 7 clamped to a section of the mandible wherein are depicted a platform top surface 7a with two cut outs 7b for the preparing of two osteotomies with the same surgical jig clamped in one location on the mandible.

FIG. 15c is a top/side angled view along the mesio-distal axis of yet another embodiment of the surgical jig 7 clamped to a section of the mandible wherein the clamping elements 30 are released and tightened onto the adjacent teeth via a threaded screw 27 that connects them and a turning handle 22 which allows for the opening and closing of the slotted clamp arms 28 which slide along a slotted track 31 that is illustrated in FIG. 15d.

FIG. 15d is a top/side view along the bucco-lingual axis of the surgical jig 7 of FIG. 15c, wherein is depicted the slotted track 31 of the surgical jig 7, the turning handles 22 of the two clamping elements 30, the adjusting knob 23 of the bony plate positioning elements 19 which are turned to slide these elements 19 along a slotted track 31a so as to orient the surgical jig 7 at the proper angle in relation to the buccal and lingual cortical plates of the jawbone and the occlusal surface of the crest of the bony ridge of the target bone site 11.

FIG. 15e is a bottom view along the bucco-lingual axis of the surgical jig 7 of FIG. 15c wherein is depicted the slotted track 31a for adjusting the bony plate positioning elements 19.

Figure 16A:
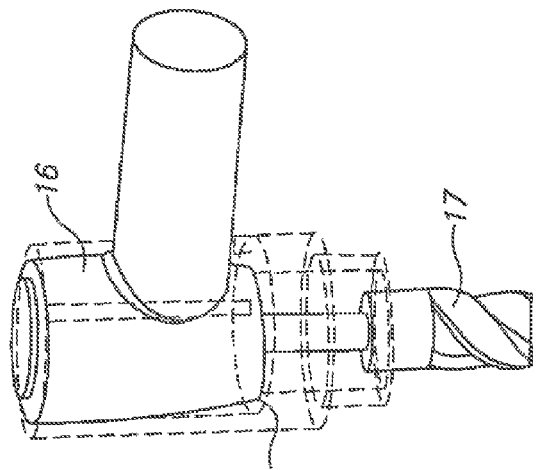
FIG. 16a is an illustrative cross-sectional sketch of a removable dental handpiece guide sleeve adaptor 14 of the present invention.

FIG. 16a is a cross-sectional sketch of one embodiment of the removable dental handpiece guide sleeve adaptor 14 of the present invention wherein are depicted the bottom ring 14f which slides over the head component drill guide ring 8a and the bore shaft drill guide ring 9a, a cut out hole 14e, a cut out 14d in the side wall of the upper ring 14a, a limiting circumferential seating ring step 14b and a depth gauge 14c of the lower ring 14c.

Figure 16B:
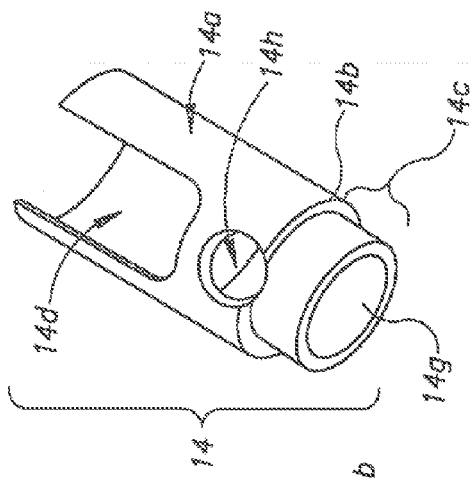

FIG. 16b is an angled front view of the embodiment of the removable dental handpiece guide sleeve adaptor of FIG. 16a wherein are depicted the same features as in FIG. 16a the inner limiting seating ring 14h onto which the head 16a of the handpiece 16 rests and the ring hole 14g.

Figure 16C:
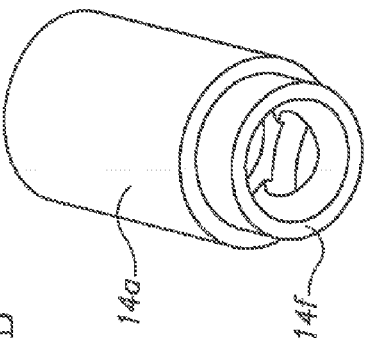
FIG. 16c is an illustrative angled bottom view of the removable dental handpiece guide sleeve adaptor 14 of FIG. 16b.

FIG. 16c is an angled bottom view of the embodiment of the removable dental handpiece guide sleeve adaptor 14 of FIG. 16b wherein are depicted the upper ring 14a and the terminal lip 14f of the lower ring 14c.

Figure 16D:
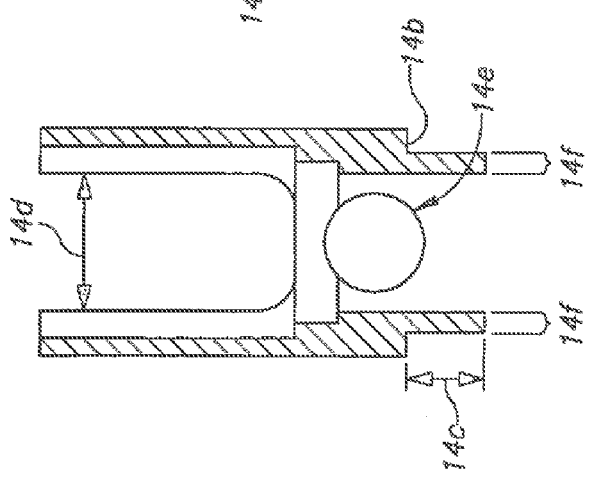
FIG. 16d is an illustrative "see-through" side view of the working end (head) of a dental handpiece 16 inserted into a handpiece guide sleeve adaptor 14.

FIG. 16d is a "see-through" side view of the working end (head) of the dental handpiece 16 inserted into one embodiment of the handpiece guide sleeve adaptor 14 of the present invention.

FIG. 17a is a cross-sectional sketch of one embodiment of the bore shaft depth template of the present invention wherein are depicted the bottom surface 34g, the shaft 34a, the knob handle 34f, graduated depth gauge markers, 34c, 34d, 34e, and the bore shaft template end 34b.

FIG. 17b is an angled front view of the embodiment of the head component template 35 wherein are depicted the handle 35a, and the template end 35b.

FIG. 17c is an angled front view of one embodiment of the head component-root screw depth template 36 of the present invention wherein are depicted the cut outs 36c for checking if the root screw top ends 1f are at the same height in their respective bore shafts 15b.

FIG. 17d is side view of the head component template 35 of FIG. 17b wherein is depicted the bottom surface 35c for checking how level the bony floor 33 of the upper section 15a is.

FIG. 17e is a cross-sectional sketch of one embodiment of the head component root screw depth template 36 of FIG. 17c wherein are depicted the template end 36b, and the cut outs 36c.

While the present invention has been described primarily with respect to dental implants, the scope of the present invention may include implants designed for other parts of the anatomy, for example, the spinal column, the hip, or shoulder.

The foregoing description of the embodiments of the invention has been presented for the purposes of illustration and description. It is not intended to be exhaustive or to limit the invention to the precise form disclosed. It should be appreciated by persons skilled in the art that many modifications, variations, substitutions, changes, and equivalents are possible in light of the above teaching. It is, therefore, to be understood that the appended claims are intended to cover all such modifications and changes as fall within the true spirit of the invention.

What is claimed is:

1. A bone implant comprising
   i. a head component for securing the implant into a bone, wherein the head component has a proximal end and distal end and is adapted along its entire length to be implanted entirely in the bone, wherein the proximal end has a long direction and a short direction both orthogonal to the length of the head component, and the head component is adapted for orienting the long direction parallel to a long axis of the bone;
   ii. one or more bone attachment components including a first bone attachment component, each independent of and separate from the head component for securing the implant into a bone, wherein each bone attachment component has a proximal end and a distal end and is adapted along its entire length to be implanted in the bone and includes an internally threaded bore hole for receiving a connector component;

wherein the head component is further adapted to be secured to each of the bone attachment components with the connector components at the time of initial implantation of the bone attachment component and the head component into the bone; and wherein the first bone attachment component oriented at a tilt angle to the proximal end of the head component is secured to the head component at the tilt angle, wherein the tilt angle is an acute angle between the length direction of the head component and an axis of rotation of the first bone attachment component; and iii. an abutment adapted to be secured independently to the head component in an overlying relation to the head component;

wherein the head component has one or more bore holes, wherein each bore hole is divided into two or more sections including:

an upper bore hole section having a generally vertical orientation aligned with a length direction of the head component, wherein the length direction is orthogonal to the short direction and the long direction; and a lower bore hole section oriented at a tilt angle relative to the orientation of the upper bore hole section, and which includes an internal limiting flange within a proximal end of the lower bore hole section, wherein the internal limiting flange is oriented at a corresponding angle to the lower bore hole section for enabling the connector component to securely fasten the bone attachment component to the head component at the tilt angle.

2. The bone implant of claim 1, wherein the proximal end of the head component has an undersurface and includes one or more set rings angled relative to the undersurface of the head component's exterior proximal surface, wherein each set ring allows for an intimate seating of the distal end of one of the bone attachment components at the tilt angle to the under surface of the proximal end of the head component.

3. The bone implant of claim 2, wherein the angled set ring is substantially spherical in contour, and wherein the distal end of the bone attachment component is substantially spherical in contour, the respective contours being adapted to provide a ball and socket coupling of the distal end of the bone attachment component to the set ring.

4. The bone implant of claim 2, wherein at least one upper bore hole section of the one or more bore holes is internally threaded for securing an abutment component to the bone implant.

5. The bone implant of claim 4, wherein the head component includes two or more bore holes having lower sections that are not parallel to each other.

6. The bone implant of claim 5, wherein the bone implant comprises two or more bone attachment components including two bone attachment components having longitudinal axes that are not parallel.

7. The bone implant of claim 2, wherein the angled internal limiting flange of the lower bore hole section of the head component has a distal surface and separates the distal head of the connector component from the bone attachment component and allows for the secure seating of the distal head of the connector component on the distal surface of the angled internal limiting flange.

8. The bone implant of claim 1, wherein the bone implant is a dental implant and the tilt angle is an acute angle of 0.5° or more.

9. The bone implant of claim 1, wherein each bone attachment component has a distal end and the head component has a proximal surface for mating with the distal end of the bone attachment component, wherein the bone implant includes one or more first connector components, wherein each first connector component secures one of the one or more bone attachment components to the head component in an angled relation to the head component, so that the proximal surface of the head component rests on the distal ends of the respective angled one or more bone attachment components.

10. The bone implant of claim 1, wherein the implant includes an oval head component and wherein the abutment is shaped to conform to the shape of the head component.

11. The bone implant of claim 1, wherein the head component is attached to the abutment component, wherein the abutment component has one or more bore holes aligned with the upper section of the bore hole(s) of the head component.

12. The bone implant of claim 1, the bone attachment is a root screw having an externally threaded shaft for screwing into a bone, wherein the diameter of the externally threaded shaft is greater than the diameter of the one or more bore holes of the head component in the proximal region of the head component where the head component rests on a distal end of the root screw.

13. The bone implant of claim 1, wherein the abutment is secured to the head component by a plurality of connectors, so as to secure the abutment to the head component in a substantially rotation-free fit relative to the head component.

14. A bone implant comprising:
i. a head component for securing the implant into a bone, wherein the head component has a proximal end and distal end and is adapted along its entire length to be implanted entirely in the bone, wherein the proximal end has a long direction and a short direction both orthogonal to the length of the head component, and the head component is adapted for orienting the long direction parallel to a long axis of the bone;
ii. one or more bone attachment components including a first bone attachment component, each independent of and separate from the head component for securing the implant into a bone, wherein each bone attachment component has a proximal end and a distal end and is adapted along its entire length to be implanted in the bone and includes an internally threaded bore hole for receiving a connector component;

wherein the head component is further adapted to be secured to each of the bone attachment components with the connector components at the time of initial implantation of the bone attachment component and the head component into the bone; and wherein the first bone attachment component oriented at a tilt angle to the proximal end of the head component is secured to the head component at the tilt angle, wherein the tilt angle is an acute angle between the length direction of the head component and an axis of rotation of the first bone attachment component; and iii. an abutment adapted to be secured independently to the head component in an overlying relation to the head component;

wherein each of the one or more bone attachment components has a distal neck with a convex collar surrounding the neck, wherein the neck has a lip region that surrounds the internally threaded bore hole of each of the one or more bone attachment components, and the neck has an external petal shaped locking feature incorporated on the lip region;

the head component includes a bore hole for attaching the head component to one of the one or more bone attachment components using the connector component;

wherein the neck of the bone attachment component inserts into the bore hole of the head component and the convex collar of the neck seats onto a matching concave proximal mating surface of the internal limiting flange of the bore hole of the head component while the petal shaped locking feature on the neck of each of the one or more bone attachment components extends beyond the limiting flange and couples with a matching petal shaped locking feature incorporated in the bore hole of the head component above the limiting concave flange.

15. The bone implant of claim 14, wherein the head component has one or more bore holes, wherein each bore hole is divided into two or more sections including:

i. an upper bore hole section having a generally vertical orientation aligned with a length direction of the head component, wherein the length direction is orthogonal to the short direction and the long direction; and ii. a lower bore hole section oriented at a tilt angle relative to the orientation of the upper bore hole section, and which includes an internal limiting flange within a proximal end of the lower bore hole section, wherein the internal limiting flange is oriented at a corresponding angle to the lower bore hole section for enabling the connector component to securely fasten the bone attachment component to the head component at the tilt angle.

* * * * *